United States Patent
Bellin et al.

(10) Patent No.: US 9,377,428 B2
(45) Date of Patent: Jun. 28, 2016

(54) NON-DESTRUCTIVE LEACHING DEPTH MEASUREMENT USING CAPACITANCE SPECTROSCOPY

(71) Applicant: Varel International Ind., L.P., Carrollton, TX (US)

(72) Inventors: Federico Bellin, Tomball, TX (US); Vamsee Chintamaneni, Houston, TX (US)

(73) Assignee: VAREL INTERNATIONAL IND., L.P., Carrollton, TX (US)

( * ) Notice: Subject to any disclaimer, the term of this patent is extended or adjusted under 35 U.S.C. 154(b) by 0 days.

(21) Appl. No.: 14/286,136

(22) Filed: May 23, 2014

(65) Prior Publication Data

US 2014/0253149 A1  Sep. 11, 2014

Related U.S. Application Data

(63) Continuation-in-part of application No. 13/401,188, filed on Feb. 21, 2012.

(51) Int. Cl.
  *G01N 27/22* (2006.01)
  *G01N 33/40* (2006.01)

(52) U.S. Cl.
  CPC ............... *G01N 27/22* (2013.01); *G01N 33/40* (2013.01)

(58) Field of Classification Search
  CPC .................................................. G01N 27/22
  See application file for complete search history.

(56) References Cited

U.S. PATENT DOCUMENTS

| 2,755,240 A | 7/1956 | Normore et al. |
|---|---|---|
| 2,934,811 A | 5/1960 | C. L. Wellington |
| 4,255,976 A | 3/1981 | Formato |
| 4,290,016 A | 9/1981 | Lorenzi |
| 4,952,869 A | 8/1990 | Tuttle |

(Continued)

FOREIGN PATENT DOCUMENTS

| DE | 102005040296 | 2/2007 |
|---|---|---|
| WO | 2013003333 | 1/2013 |

OTHER PUBLICATIONS

Translation of Description of WO/2007022749 corresponding to International Application No. PCT/DE2006/001376 "Measuring Method for In-Situ Control of the Chemical Etching Process of Latent Ion Tracks in a Dielectric Substrate" printed on Nov. 14, 2004, 4 pages, http://patentscope.wipo.int/search/en/detail/jsf, unofficial translation via Google translate.

Gill Jennings & Avery LLP, Henry Hunt-Grubbe, Response to extended European Search Report (EESR) issued in European Patent Application No. 13156142.5, dated Oct. 30, 2014, 25 pages.

(Continued)

*Primary Examiner* — Tung X Nguyen
*Assistant Examiner* — Feba Pothen

(57) ABSTRACT

A method of characterizing a quality of a polycrystalline diamond compact (PDC) cutter includes obtaining a PDC cutter that includes a leached layer and an unleached layer. The unleached layer is positioned adjacent to the leached layer, and the leached layer has at least a portion of a catalyst material removed from therein. The method further includes measuring capacitance values of the PDC cutter at multiple frequencies of an electrical signal provided to the PDC cutter by a capacitance measuring device to measure the capacitance values of the PDC cutter. The method also includes characterizing a quality of the PDC cutter based on a lowest capacitance value from among the capacitance values. Each capacitance value of the capacitance values is measured at a respective frequency of the multiple frequencies of the electrical signal.

14 Claims, 12 Drawing Sheets

(56) References Cited

U.S. PATENT DOCUMENTS

| | | | |
|---|---|---|---|
| 6,063,333 A | | 5/2000 | Dennis |
| 6,107,808 A | * | 8/2000 | McKee et al. ............... 324/548 |
| 6,388,453 B1 | * | 5/2002 | Greer ........................... 324/667 |
| 6,437,579 B1 | | 8/2002 | Yamashita et al. |
| 7,558,369 B1 | | 7/2009 | Mourik et al. |
| 7,616,734 B1 | | 11/2009 | Corbett et al. |
| 7,712,553 B2 | | 5/2010 | Shamburger |
| 7,757,792 B2 | | 7/2010 | Shamburger |
| 8,014,492 B1 | | 9/2011 | Corbett et al. |
| 8,080,074 B2 | | 12/2011 | Sani |
| 2002/0053904 A1 | | 5/2002 | Chen et al. |
| 2002/0179864 A1 | | 12/2002 | Fielden |
| 2005/0050801 A1 | | 3/2005 | Cho et al. |
| 2006/0192568 A1 | | 8/2006 | Pasero et al. |
| 2006/0244443 A1 | | 11/2006 | Goldfine et al. |
| 2007/0079994 A1 | | 4/2007 | Middlemiss |
| 2007/0131458 A1 | * | 6/2007 | Shen et al. .................... 175/374 |
| 2007/0169419 A1 | | 7/2007 | Davis et al. |
| 2008/0054891 A1 | | 3/2008 | Dobsky |
| 2008/0104034 A1 | | 5/2008 | Stewart et al. |
| 2008/0121433 A1 | * | 5/2008 | Ledgerwood ................ 175/327 |
| 2008/0164887 A1 | * | 7/2008 | Schr der ........................ 324/668 |
| 2008/0185189 A1 | | 8/2008 | Griffo et al. |
| 2008/0223623 A1 | | 9/2008 | Keshavan et al. |
| 2008/0241024 A1 | * | 10/2008 | Riekkola-Vanhanen et al. ............................... 423/27 |
| 2008/0290866 A1 | | 11/2008 | Cuffe et al. |
| 2009/0152018 A1 | | 6/2009 | Sani |
| 2009/0173015 A1 | | 7/2009 | Keshavan et al. |
| 2010/0011673 A1 | | 1/2010 | Shamburger |
| 2010/0095602 A1 | | 4/2010 | Belnap et al. |
| 2010/0155149 A1 | | 6/2010 | Keshavan et al. |
| 2010/0231208 A1 | | 9/2010 | Huggett et al. |
| 2010/0292604 A1 | * | 11/2010 | Kapon et al. ......... A61B 5/0535 600/547 |
| 2011/0120782 A1 | * | 5/2011 | Cooley et al. ................. 175/432 |
| 2011/0215814 A1 | * | 9/2011 | Dorrough ..................... 324/663 |
| 2011/0258936 A1 | | 10/2011 | DiGiovanni |
| 2012/0047815 A1 | | 3/2012 | Sani |
| 2012/0055717 A1 | | 3/2012 | Liversage et al. |
| 2012/0067652 A1 | | 3/2012 | Bellin |
| 2012/0211284 A1 | | 8/2012 | DiGiovanni |
| 2012/0241224 A1 | | 9/2012 | Qian et al. |
| 2013/0001100 A1 | | 1/2013 | Thigpen et al. |
| 2013/0213433 A1 | | 8/2013 | Bellin et al. |
| 2013/0213720 A1 | | 8/2013 | Bellin et al. |
| 2013/0214768 A1 | | 8/2013 | Chintamaneni et al. |
| 2013/0214769 A1 | | 8/2013 | King et al. |
| 2013/0214799 A1 | | 8/2013 | Bellin et al. |
| 2013/0247478 A1 | | 9/2013 | Bellin et al. |
| 2013/0248258 A1 | | 9/2013 | Bellin et al. |
| 2014/0062509 A1 | | 3/2014 | Bellin et al. |

OTHER PUBLICATIONS

Copenheaver, Blaine R, International Search Report and Written Opinion of the International Searching Authority for PCT/US2013/026918, Apr. 23, 2013, pp. 1-11.

Copenheaver, Blaine R, International Search Report and Written Opinion of the International Searching Authority for PCT/US2013/026931, Apr. 26, 2013, pp. 1-10.

Copenheaver, Blaine R, International Search Report and Written Opinion of the International Searching Authority for PCT/US2013/026938, Apr. 25, 2013, pp. 1-13.

Grove et al., Determining Dielectric Constants Using a Parallel Plate Capacitor, American Journal of Physics 73 (1), Jan. 2005, entire document. [retrieved on Apr. 4, 2013]. Retrieved form Internet <URL: http://users.df.uba.ar/sgil/physics_paper_doc/papers_phys/e&m/dielectr_const_2k4.pdf>entire document.

Bellin et al., "The Current State of PDC Bit Technology Part 2 of 3: Leaching a Thin Layer at the Working Surface of a PDC Cutter to Remove the Cobalt Dramatically Reduces Diamond Degradation Due to Frictional Heat", Oct. 1, 2010, pp. 1-18, Retrieved from the Internet: URL: http://www.varelintl.com/content/includes/world_oil_october 2010.pdf [retrieved on Mar. 18, 2014].

Bellin et al., "The Current State of PDC Bit Technology Part 2 of 3: Improvements in Material Properties and Testing Methods Are Being Pursued to Make PDC the Cutter of Choice for an Increasing Variety of Applications" Nov. 1, 2010, pp. 67-71, Retrieved from the Internet: URL: http://www.varelintl.com/content/includes/pdc_technology_part_3.pdf.

Pierson, Hugh O., Chapter 12: Natural High-Pressure Synthetic Diamond, Handbook of Carbon, Graphite, Diamond and Fullerences, Properties, Processing and Applications, Jan. 1, 1993, pp. 278-301, Noyes Publications.

Kraus, Leonie, European Search Report EP Application No. 13156142, Mar. 19, 2014, 7 pages, place of search The Hague.

Kraus, Leonie, European Search Report EP Application No. 13156143, Feb. 19, 2014, 6 pages, place of search The Hague.

Thomas, Shane, International Search Report and Written Opinion issued in PCT/US2014/064359, completed on Jan. 18, 2015, 11 pages, United States Patent and Trademark Office, Alexandria, Virginia, United States.

Forestier, Gilles, European Search Report issued in European Patent Application No. 13156140.9,completed on Jan. 12, 2015, 8 pages, European Patent Office, The Hague.

Forestier, Gilles, European Search Report issued in European Patent Application No. 13156138.3, completed on Jan. 12, 2015, 8 pages, European Patent Office, The Hague.

Copenheaver, Blain, International Search Report and Written Opinion issued in international application No. PCT/US2015/028308, completed Jul. 2, 2015, mailed Jul. 29, 2015, 10 pages, United States Patent and Trademark Office, Alexandria, Virginia, United States.

* cited by examiner

NON-DESTRUCTIVE LEACHING DEPTH MEASUREMENT USING CAPACITANCE SPECTROSCOPY

CROSS REFERENCE TO RELATED APPLICATIONS

The present application is a continuation-in-part of and claims priority to U.S. patent application Ser. No. 13/401,188, entitled "Use Of Capacitance To Analyze Polycrystalline Diamond" and filed on Feb. 21, 2012, which is incorporated herein by reference.

TECHNICAL FIELD

The present invention relates generally to a method and apparatus for measuring characteristics of one or more regions within an ultra-hard polycrystalline structure; and more particularly, to a non-destructive method and apparatus for measuring the leaching depth within the ultra-hard polycrystalline structure and/or characterizing at least a portion of the ultra-hard polycrystalline structure, such as the ones used in forming polycrystalline diamond compact ("PDC") cutters, using at least capacitance measurements.

BACKGROUND

Polycrystalline diamond compacts ("PDC") have been used in industrial applications, including rock drilling applications and metal machining applications. Such compacts have demonstrated advantages over some other types of cutting elements, such as better wear resistance and impact resistance. The PDC can be formed by sintering individual diamond particles together under the high pressure and high temperature ("HPHT") conditions referred to as the "diamond stable region," which is typically above forty kilobars and between 1,200 degrees Celsius and 2,000 degrees Celsius, in the presence of a catalyst/solvent which promotes diamond-diamond bonding. Some examples of catalyst/solvents for sintered diamond compacts are cobalt, nickel, iron, and other Group VIII metals. PDCs usually have a diamond content greater than seventy percent by volume, with about eighty percent to about ninety-eight percent being typical. An unbacked PDC can be mechanically bonded to a tool (not shown), according to one example. Alternatively, the PDC is bonded to a substrate, thereby forming a PDC cutter, which is typically insertable within a downhole tool (not shown), such as a drill bit or a reamer.

FIG. 1 shows a side view of a PDC cutter 100 having a polycrystalline diamond ("PCD") cutting table 110, or compact, in accordance with the prior art. Although a PCD cutting table 110 is described in the exemplary embodiment, other types of cutting tables, including polycrystalline boron nitride ("PCBN") compacts, are used in alternative types of cutters. Referring to FIG. 1, the PDC cutter 100 typically includes the PCD cutting table 110 and a substrate 150 that is coupled to the PCD cutting table 110. The PCD cutting table 110 is about one hundred thousandths of an inch (2.5 millimeters) thick; however, the thickness is variable depending upon the application in which the PCD cutting table 110 is to be used.

The substrate 150 includes a top surface 152, a bottom surface 154, and a substrate outer wall 156 that extends from the circumference of the top surface 152 to the circumference of the bottom surface 154. The PCD cutting table 110 includes a cutting surface 112, an opposing surface 114, and a PCD cutting table outer wall 116 that extends from the circumference of the cutting surface 112 to the circumference of the opposing surface 114. The opposing surface 114 of the PCD cutting table 110 is coupled to the top surface 152 of the substrate 150. Typically, the PCD cutting table 110 is coupled to the substrate 150 using a high pressure and high temperature ("HPHT") press. However, other methods known to people having ordinary skill in the art can be used to couple the PCD cutting table 110 to the substrate 150. In one embodiment, upon coupling the PCD cutting table 110 to the substrate 150, the cutting surface 112 of the PCD cutting table 110 is substantially parallel to the substrate's bottom surface 154. Additionally, the PDC cutter 100 has been illustrated as having a right circular cylindrical shape; however, the PDC cutter 100 is shaped into other geometric or non-geometric shapes in other exemplary embodiments. In certain exemplary embodiments, the opposing surface 114 and the top surface 152 are substantially planar; however, the opposing surface 114 and the top surface 152 are non-planar in other exemplary embodiments. Additionally, according to some exemplary embodiments, a bevel (not shown) is formed around at least the circumference of the cutting surface 112.

According to one example, the PDC cutter 100 is formed by independently forming the PCD cutting table 110 and the substrate 150, and thereafter bonding the PCD cutting table 110 to the substrate 150. Alternatively, the substrate 150 is initially formed and the PCD cutting table 110 is subsequently formed on the top surface 152 of the substrate 150 by placing polycrystalline diamond powder onto the top surface 152 and subjecting the polycrystalline diamond powder and the substrate 150 to a high temperature and high pressure process. Alternatively, the substrate 150 and the PCD cutting table 110 are formed and bonded together at about the same time. Although a few methods of forming the PDC cutter 100 have been briefly mentioned, other methods known to people having ordinary skill in the art can be used.

According to one example for forming the PDC cutter 100, the PCD cutting table 110 is formed and bonded to the substrate 150 by subjecting a layer of diamond powder and a mixture of tungsten carbide and cobalt powders to HPHT conditions. The cobalt is typically mixed with tungsten carbide and positioned where the substrate 150 is to be formed. The diamond powder is placed on top of the cobalt and tungsten carbide mixture and positioned where the PCD cutting table 110 is to be formed. The entire powder mixture is then subjected to HPHT conditions so that the cobalt melts and facilitates the cementing, or binding, of the tungsten carbide to form the substrate 150. The melted cobalt also diffuses, or infiltrates, into the diamond powder and acts as a catalyst for synthesizing diamond bonds and forming the PCD cutting table 110. Thus, the cobalt acts as both a binder for cementing the tungsten carbide and as a catalyst/solvent for sintering the diamond powder to form diamond-diamond bonds. The cobalt also facilitates in forming strong bonds between the PCD cutting table 110 and the cemented tungsten carbide substrate 150.

Cobalt has been a preferred constituent of the PDC manufacturing process. Traditional PDC manufacturing processes use cobalt as the binder material for forming the substrate 150 and also as the catalyst material for diamond synthesis because of the large body of knowledge related to using cobalt in these processes. The synergy between the large bodies of knowledge and the needs of the process have led to using cobalt as both the binder material and the catalyst material. However, as is known in the art, alternative metals, such as iron, nickel, chromium, manganese, and tantalum, and other suitable materials, can be used as a catalyst for diamond synthesis. When using these alternative materials as a catalyst for diamond synthesis to form the PCD cutting table 110, cobalt, or some other material such as nickel chrome or iron, is typically used as the binder material for cementing the tungsten carbide to form the substrate 150. Although some materials, such as tungsten carbide and cobalt, have been provided as examples, other materials known to people having ordinary skill in the art can be used to form the substrate 150, the PCD cutting table 110, and the bonds between the substrate 150 and the PCD cutting table 110.

FIG. 2 is a schematic microstructural view of the PCD cutting table 110 of FIG. 1 in accordance with the prior art. Referring to FIGS. 1 and 2, the PCD cutting table 110 has diamond particles 210 bonded to other diamond particles 210, one or more interstitial spaces 212 formed between the diamond particles 210, and cobalt 214, or some other catalyst, deposited within one or more of the interstitial spaces 212. During the sintering process, the interstitial spaces 212, or voids, are formed between the carbon-carbon bonds and are located between the diamond particles 210. The diffusion of cobalt 214 into the diamond powder results in cobalt 214 being deposited within these interstitial spaces 212 that are formed within the PCD cutting table 110 during the sintering process.

Once the PCD cutting table 110 is formed and placed into operation, the PCD cutting table 110 is known to wear quickly when the temperature reaches a critical temperature. This critical temperature is about 750 degrees Celsius and is reached when the PCD cutting table 110 is cutting rock formations or other known materials. The high rate of wear is believed to be caused by the differences in the thermal expansion rate between the diamond particles 210 and the cobalt 214 and also by the chemical reaction, or graphitization, that occurs between cobalt 214 and the diamond particles 210. The coefficient of thermal expansion for the diamond particles 210 is about $1.0 \times 10^{-6}$ millimeters$^{-1} \times$Kelvin$^{-1}$ ("mm$^{-1}$K$^{-1}$"), while the coefficient of thermal expansion for the cobalt 214 is about $13.0 \times 10^{-6}$ mm$^{-1}$K$^{-1}$. Thus, the cobalt 214 expands much faster than the diamond particles 210 at temperatures above this critical temperature, thereby making the bonds between the diamond particles 210 unstable. The PCD cutting table 110 becomes thermally degraded at temperatures above about 750 degrees Celsius and its cutting efficiency deteriorates significantly.

Efforts have been made to slow the wear of the PCD cutting table 110 at these high temperatures. These efforts include performing a leaching process on the PCD cutting table 110, which removes some of the cobalt 214 from the interstitial spaces 212. These leaching processes, which includes, but is not limited to, an acid leaching process and/or an electrolytic leaching process, is known to persons having ordinary skill in the art and is not described herein for the sake of brevity. By removing some of the cobalt 214, or catalyst, from the PCD cutting table 110, the thermal degradation of the PCD structure is reduced.

FIG. 3 shows a cross-section view of a leached PDC cutter 300 having a PCD cutting table 310 that has been at least partially leached in accordance with the prior art. Referring to FIG. 3, the PDC cutter 300 includes the PCD cutting table 310 coupled to a substrate 350. The substrate 350 is similar to substrate 150 (FIG. 1) and is not described again for the sake of brevity. The PCD cutting table 310 is similar to the PCD cutting table 110 (FIG. 1), but includes a leached layer 354 and an unleached layer 356. The leached layer 354 extends from the cutting surface 312, which is similar to the cutting surface 112 (FIG. 1), towards an opposing surface 314, which is similar to the opposing surface 114 (FIG. 1). In the leached layer 354, at least a portion of the cobalt 214 has been removed from within the interstitial spaces 212 (FIG. 2) using at least one leaching process mentioned above. Thus, the leached layer 354 has been leached to a desired depth 353. However, during the leaching process, one or more by-product materials 398 are formed and deposited within some of the interstitial spaces 212 (FIG. 2) in the leached layer 354. The unleached layer 356 is similar to the PCD cutting table 150 (FIG. 1) and extends from the end of the leached layer 354 to the opposing surface 314. In the unleached layer 356, the cobalt 214 (FIG. 2) remains within the interstitial spaces 212 (FIG. 2). Although a boundary line 355 is formed between the leached layer 354 and the unleached layer 356 and is depicted as being substantially linear, the boundary line 355 can be non-linear.

The leached PDC cutters 300 are leached to different desired depths 353 and how deep the cutter 300 has been leached has an effect on the performance of the cutter 300. Conventionally, the leached depth 353 of the cutter 300 is measured, or determined, by cutting the cutter 300 vertically in half and then subsequently polishing the cutter 300. The leached depth 353 is visually measured under a microscope or similar magnifying device. This process is rather tedious and cumbersome as it involves cutting the cutter 300, such as by electrical discharge machining ("EDM"), mounting, grinding, and polishing the cutter 300, and performing an analysis under a microscope. Additionally, this process destroys the cutter 300 from subsequently being used. The leached depth 353 that is determined in this manner is assumed to be the same leached depth in other cutters that were leached in the same batch.

SUMMARY

In general, the present disclosure relates to characterizing at least a portion of the ultra-hard polycrystalline structure, such as the ones used in forming polycrystalline diamond compact ("PDC") cutters, using at least capacitance measurements. In an example embodiment, a method of characterizing a quality of a polycrystalline diamond compact (PDC) cutter includes obtaining a PDC cutter that includes a leached layer and an unleached layer. The unleached layer is positioned adjacent to the leached layer, and the leached layer has at least a portion of a catalyst material removed from therein. The method further includes measuring capacitance values of the PDC cutter at multiple frequencies of an electrical signal provided to the PDC cutter by a capacitance measuring device to measure the capacitance values of the PDC cutter. The method also includes characterizing a quality of the PDC cutter based on a lowest capacitance value from among the capacitance values. Each capacitance value of the capacitance values is measured at a respective frequency of the multiple frequencies of the electrical signal.

In another example embodiment, a method of characterizing a quality of a polycrystalline structure includes obtaining a leached component comprising a polycrystalline structure. The polycrystalline structure comprises a leached layer and an unleached layer. The unleached layer is positioned adjacent to the leached layer. The leached layer has at least a portion of a catalyst material removed from therein. The method further includes measuring capacitance values of the leached component at multiple frequencies of an electrical signal. The electrical signal is provided to the leached component by a capacitance measuring device to measure capacitance of the leached component. The method also includes characterizing a quality of the leached component based on a lowest capacitance value from among the capacitance values.

Each capacitance value of the capacitance values is measured at a respective frequency of the multiple frequencies of the electrical signal.

In another example embodiment, a system for measuring capacitance of a polycrystalline diamond compact (PDC) cutter includes a capacitance measuring device that includes a first terminal and a second terminal. The system further includes a PDC cutter that has a leached layer and an unleached layer adjacent to the leached layer. The leached layer has at least a portion of a catalyst material removed from therein. The system also includes a first wire electrically coupling the first terminal to a first surface of the PDC cutter. The system further includes a second wire electrically coupling the second terminal to a second surface of the PDC cutter. The first surface and the second surface are on opposite sides of the leached layer. The second surface is a surface of the leached layer. The capacitance measuring device provides an electrical signal to the PDC cutter to measure capacitance values of the PDC cutter. The capacitance measuring device measures the capacitance values of the PDC cutter at multiple frequencies of the electrical signal.

These and other aspects, objects, features, and embodiments will be apparent from the following description and the claims.

BRIEF DESCRIPTION OF THE DRAWINGS

The foregoing and other features and aspects of the invention are best understood with reference to the following description of certain exemplary embodiments, when read in conjunction with the accompanying drawings, wherein.

Figure 1:
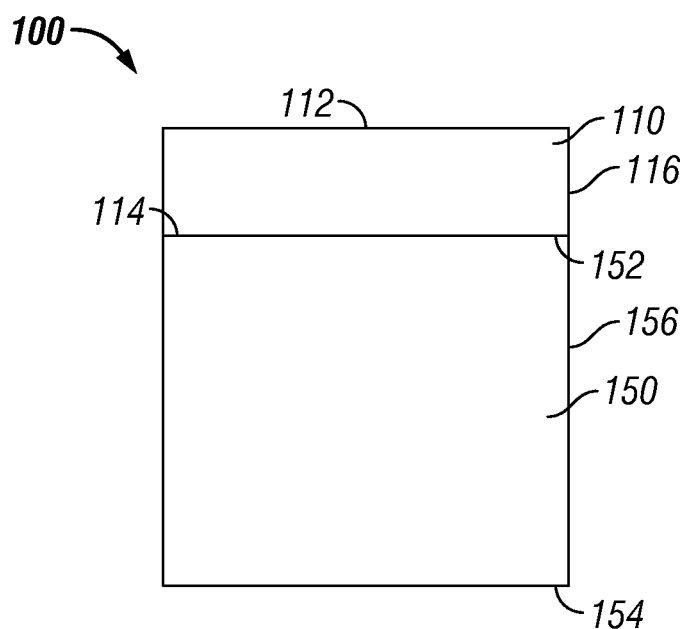
FIG. 1 is a side view of a PDC cutter having a polycrystalline diamond cutting table, or compact, in accordance with the prior art.
Figure 2:
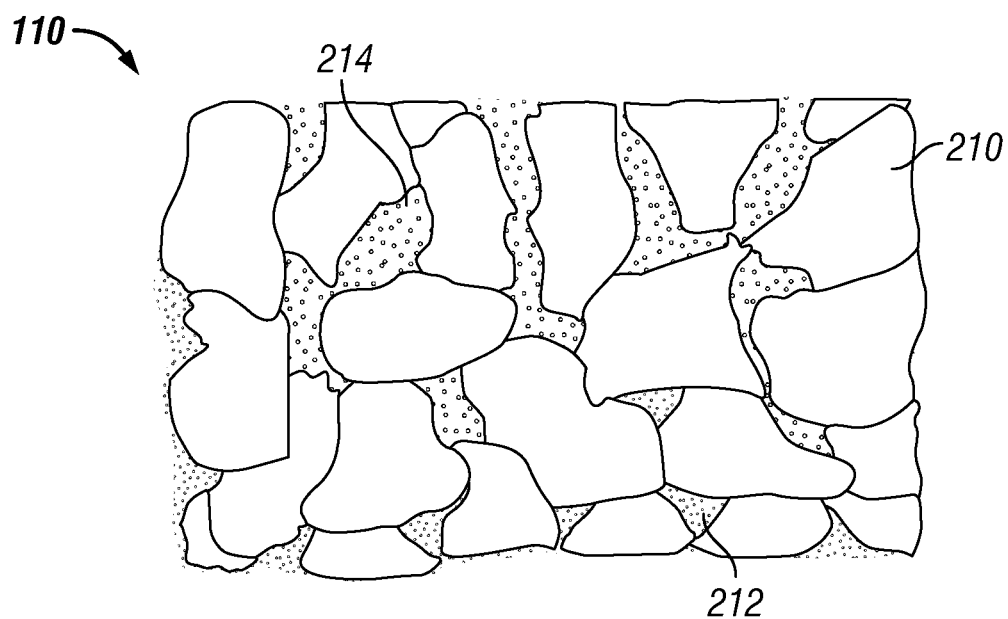
FIG. 2 is a schematic microstructural view of the PCD cutting table of FIG. 1 in accordance with the prior art.

The drawings illustrate only exemplary embodiments of the invention and are therefore not to be considered limiting of its scope, as the invention may admit to other equally effective embodiments.

DESCRIPTION OF EXEMPLARY EMBODIMENTS

The present invention is directed to a non-destructive method and apparatus for measuring the leaching depth within an ultra-hard polycrystalline structure and/or characterizing at least a portion of the ultra-hard polycrystalline structure, such as the ones used in forming polycrystalline diamond compact ("PDC") cutters, using at least capacitance measurements. Although the description of exemplary embodiments is provided below in conjunction with a PDC cutter, alternate embodiments of the invention may be applicable to other types of polycrystalline structures including, but not limited to, PCBN cutters. Further, according to some exemplary embodiments, one or more portions of the methods described below are implemented using an electronic measuring device. For example, the capacitance is measured using a capacitance measuring device. The invention is better understood by reading the following description of non-limiting, exemplary embodiments with reference to the attached drawings, wherein like parts of each of the figures are identified by like reference characters, and which are briefly described as follows.

Figure 3:
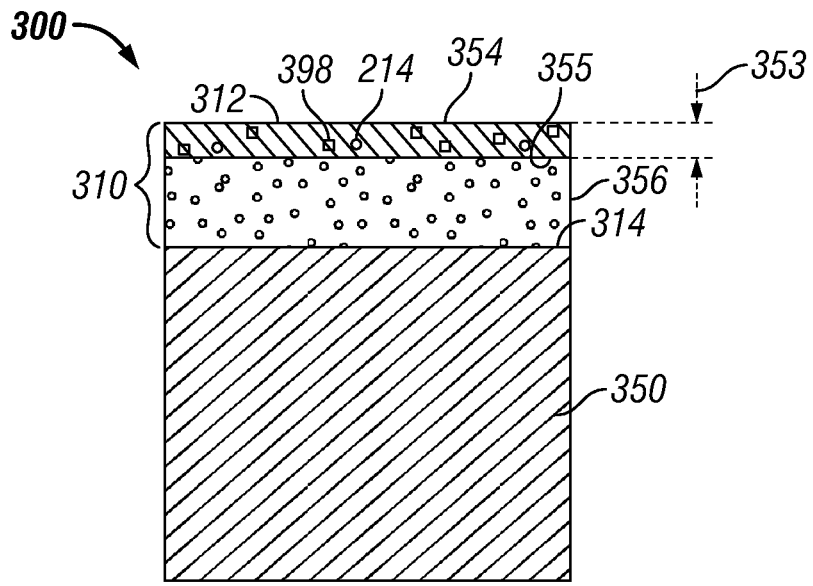
FIG. 3 is a cross-section view of a PDC cutter having a PCD cutting table that has been at least partially leached in accordance with the prior art.
Figure 4:
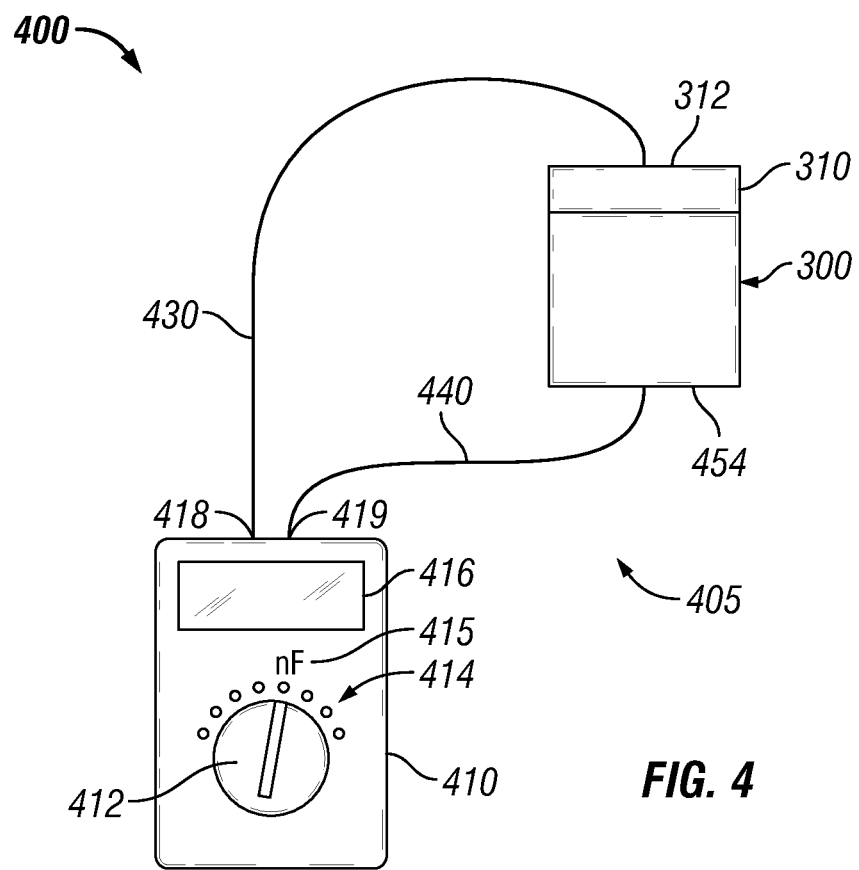
FIG. 4 is a schematic view of a capacitance measuring system in accordance to one exemplary embodiment of the present invention.

FIG. 4 is a schematic view of a capacitance measuring system 400 in accordance with one exemplary embodiment of the present invention. Referring to FIG. 4, the capacitance measuring system 400 includes a capacitance measuring device 410, the leached PDC cutter 300, a first wire 430, and a second wire 440. Although certain components have been enumerated as being included in the capacitance measuring system 400, additional components are included in other exemplary embodiments. Additionally, although the description provided below has been provided with respect to the leached PDC cutter 300, a different component, such as the PCD cutting table 310 alone or other component that includes another type of leached polycrystalline structure, is used in lieu of the leached PDC cutter 300. Additionally, although the description provided below has been provided with respect to the leached PDC cutter 300, a different component, such as a chemically cleaned leached PDC cutter (not shown), is used in lieu of the leached PDC cutter 300. The chemically cleaned leached PDC cutter has had at least a portion of the by-product materials 398 (FIG. 3) removed by using one or more processes described in related application entitled, "Method To Improve The Performance Of A Leached Cutter", which has been mentioned above and incorporated by reference herein. The leached PDC cutter 300 has been previously described with respect to FIG. 3 and is not repeated again herein for the sake of brevity.

The capacitance measuring device 410 is a device that measures the capacitance of an energy storage device, which is the leached PDC cutter 300 in the instant exemplary embodiment. Capacitance is a measure of the amount of electric potential energy stored, or separated, for a given electric potential. A common form of energy storage device is a parallel-plate capacitor. In the instant exemplary embodiment, the leached PDC cutter 300 is an example of the parallel-plate capacitor. The capacitance of the energy storage device is typically measured in farads, or nanofarads.

One example of the capacitance measuring device 410 is a multi-meter; however, other capacitance measuring devices known to people having ordinary skill in the art are used in one or more alternative exemplary embodiments. The multi-meter 410 includes a positionable dial 412, a plurality of measurement settings 414, a display 416, a positive terminal 418, and a negative terminal 419. According to some exemplary embodiments, the positionable dial 412 is rotatable in a clockwise and/or counter-clockwise manner and is set to one of several available measurement settings 414. In the instant exemplary embodiment, the positionable dial 412 is set to a nanofaraday setting 415 so that the multi-meter 410 measures capacitance values. The display 416 is fabricated using polycarbonate, glass, plastic, or other known suitable material and communicates a measurement value, such as a capacitance value, to a user (not shown) of the multi-meter 410. The positive terminal 418 is electrically coupled to one end of the first wire 430, while the negative terminal 419 is electrically coupled to one end of the second wire 440.

The first wire 430 is fabricated using a copper wire or some other suitable conducting material or alloy known to people having ordinary skill in the art. According to some exemplary embodiments, the first wire 430 also includes a non-conducting sheath (not shown) that surrounds the copper wire and extends from about one end of the copper wire to an opposing end of the cooper wire. The two ends of the copper wire are exposed and are not surrounded by the non-conducting sheath. In some exemplary embodiments, an insulating material (not shown) also surrounds the copper wire and is disposed between the copper wire and the non-conducting sheath. The insulating material extends from about one end of the non-conducting sheath to about an opposing end of the non-conducting sheath. As previously mentioned, one end of the first wire 430 is electrically coupled to the positive terminal 418, while the opposing end of the first wire 430 is electrically coupled to the cutting surface 312 of the leached PDC cutter 300. The opposing end of the first wire 430 is electrically coupled to the cutting surface 312 in one of several methods. In one example, the first wire 430 is electrically coupled to the cutting surface 312 using one or more fastening devices (not shown), such as a clamp, or using an equipment (not shown) that supplies a force to retain the first wire 430 in electrical contact with the cutting surface 312. In another example, a clamp (not shown) is coupled to the opposing end of the first wire 430 and a conducting component (not shown), such as aluminum foil, is coupled to, or placed in contact with, the cutting surface 312. The clamp is electrically coupled to the conducting component, thereby electrically coupling the first wire 430 to the cutting surface 312. Additional methods for coupling the first wire 430 to the cutting surface 312 can be used in other exemplary embodiments.

The second wire 440 is fabricated using a copper wire or some other suitable conducting material or alloy known to people having ordinary skill in the art. According to some exemplary embodiments, the second wire 440 also includes a non-conducting sheath (not shown) that surrounds the copper wire and extends from about one end of the copper wire to an opposing end of the cooper wire. The two ends of the copper wire are exposed and are not surrounded by the non-conducting sheath. In some exemplary embodiments, an insulating material (not shown) also surrounds the copper wire and is disposed between the copper wire and the non-conducting sheath. The insulating material extends from about one end of the non-conducting sheath to an opposing end of the non-conducting sheath. As previously mentioned, one end of the second wire 440 is electrically coupled to the negative terminal 419, while the opposing end of the second wire 440 is electrically coupled to a bottom surface 454, which is similar to the bottom surface 154 (FIG. 1), of the leached PDC cutter 300. The second wire 440 is electrically coupled to the bottom surface 454 in a similar manner as the first wire 430 is electrically coupled to the cutting surface 312.

Hence, a circuit 405 is completed using the multi-meter 410, the first wire 430, the leached PDC cutter 300, and the second wire 440. The current is able to flow from the positive terminal 418 of the multi-meter 410 to the cutting surface 312 of the leached PDC cutter 300 through the first wire 430. The current then flows through the leached PDC cutter 300 to the bottom surface 454 of the leached PDC cutter 300. When the multi-meter 410 is turned on, a voltage differential exists between the cutting surface 312 and the bottom surface 454. The current then flows from the bottom surface 454 to the negative terminal 419 of the multi-meter 410 through the second wire 440. The capacitance measurement of the leached PDC cutter 300 is determined when the value displayed on the display 416 reaches a peak value or remains constant for a period of time.

Figure 5:
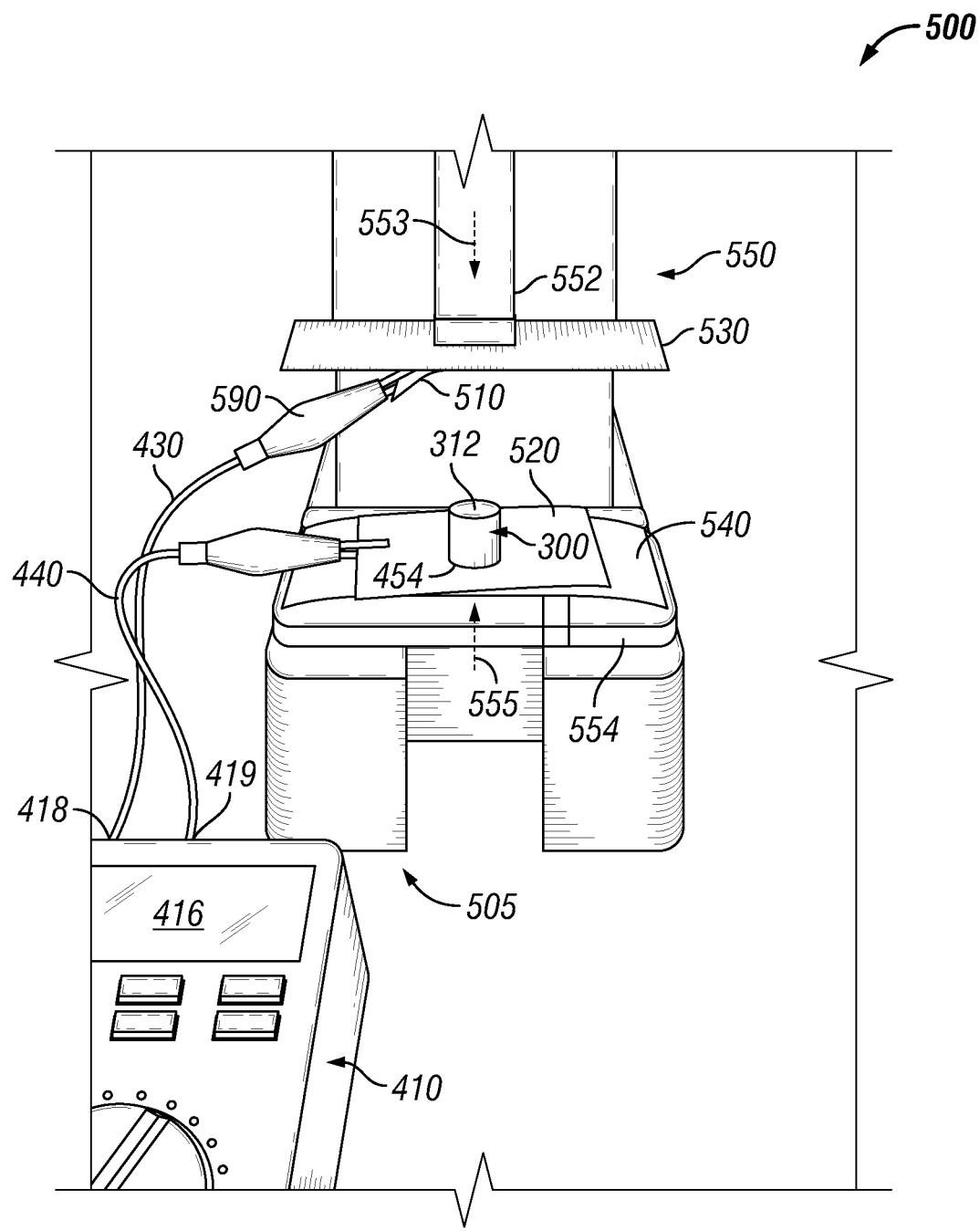
FIG. 5 is a schematic view of a capacitance measuring system in accordance to another exemplary embodiment of the present invention.

FIG. 5 is a schematic view of a capacitance measuring system 500 in accordance to another exemplary embodiment of the present invention. Referring to FIG. 5, the capacitance measuring system 500 includes the capacitance measuring device 410, the leached PDC cutter 300, the first wire 430, the second wire 440, a first conducting material 510, a second conducting material 520, a first insulating material 530, a second insulating material 540, and an Arbor Press 550. Although certain components have been enumerated as being included in the capacitance measuring system 500, additional components are included in other exemplary embodiments. Further, although certain components have been enumerated as being included in the capacitance measuring system 500, alternative components having similar functions as the enumerated components are used in alternative exemplary embodiments. Additionally, although the description provided below has been provided with respect to the leached PDC cutter 300, a different component, such as the PCD cutting table 310 (FIG. 3) alone or other component that includes another type of leached polycrystalline structure, is used in lieu of the leached PDC cutter 300. Additionally, although the description provided below has been provided with respect to the leached PDC cutter 300, a different component, such as the chemically cleaned leached PDC cutter mentioned above, is used in lieu of the leached PDC cutter 300. The capacitance measuring device 410, the leached PDC cutter 300, the first wire 430, and the second wire 440 have been previously described and are not repeated again herein for the sake of brevity.

The first conducting material 510 and the second conducting material 520 are similar to one another in certain exemplary embodiments, but are different in other exemplary embodiments. According to one exemplary embodiment, the conducting materials 510, 520 are fabricated using aluminum foil; however, other suitable conducting materials can be used. The first conducting material 510 is positioned adjacently above and in contact with the cutting surface 312. The second conducting material 520 is positioned adjacently below and in contact with the bottom surface 454. The first conducting material 510 and the second conducting material 520 provide an area to which the first wire 430 and the second wire 440, respectively, make electrical contact. Additionally, the first conducting material 510 and the second conducting material 520 assist in minimizing contact resistance with the cutting surface 312 and the bottom surface 454, respectively, which is discussed in further detail below. In certain exemplary embodiments, the first conducting material 510 and the second conducting material 520 are the same shape and size; while in other exemplary embodiments, one of the conducting materials 510, 520 is a different shape and/or size than the other conducting material 510, 520.

The first insulating material 530 and the second insulating material 540 are similar to one another in certain exemplary embodiments, but are different in other exemplary embodiments. According to one exemplary embodiment, the insulating materials 530, 540 are fabricated using paper; however, other suitable insulating materials, such as rubber, can be used. The first insulating material 530 is positioned adjacently above and in contact with the first conducting material 510. The second insulating material 540 is positioned adjacently below and in contact with the second conducting material 520. The first insulating material 530 and the second insulating material 540 provide a barrier to direct current flow only through a circuit 505, which is discussed in further detail below. In certain exemplary embodiments, the first insulating material 530 and the second insulating material 540 are the same shape and size; while in other exemplary embodiments, one of the insulating materials 530, 540 is a different shape and/or size than the other insulating material 530, 540. Additionally, in certain exemplary embodiments, the insulating materials 530, 540 is larger in size than its corresponding conducting material 510, 520. However, one or more of the insulating materials 530, 540 is either larger or smaller than its corresponding conducting material 510, 520 in alternative exemplary embodiments.

The Arbor Press 550 includes an upper plate 552 and a base plate 554. The upper plate 552 is positioned above the base plate 554 and is movable towards the base plate 554. In other exemplary embodiments, the base plate 554 is movable towards the upper plate 552. The first insulating material 530, the first conducting material 510, the leached PDC cutter 300, the second conducting material 520, and the second insulating material 540 are positioned between the upper plate 552 and the base plate 554 such that the second insulating material 540 is positioned adjacently above and in contact with the base plate 554. The upper plate 552 is moved towards the base plate 554 until the upper plate 552 applies a downward load 553 onto the cutting surface 312 of the leached PDC cutter 300. When the downward load 553 is applied, the first conducting material 510 is deformed and adapted to the rough and very stiff cutting surface 312, thereby minimizing contact resistance between the first conducting material 510 and the cutting surface 312 and greatly improving the capacitance measurement consistency. At this time, the base plate 554 also applies an upward load 555 onto the bottom surface 454 of the leached PDC cutter 300. When the upward load 555 is applied, the second conducting material 520 is deformed and adapted to the rough and very stiff bottom surface 454, thereby minimizing contact resistance between the second conducting material 520 and the bottom surface 454 and greatly improving the capacitance measurement consistency.

In certain exemplary embodiments, the downward load 553 is equal to the upward load 555. The downward load 553 and the upward load 555 is about one hundred pounds; however, these loads 553, 555 range from about two pounds to about a critical load. The critical load is a load at which the leached PDC cutter 300 is damaged when applied thereto.

In one exemplary embodiment, the second insulating material 540 is positioned on the base plate 554, the second conducting material 520 is positioned on the second insulating material 540, the leached PDC cutter 300 is positioned on the second conducting material 520, the first conducting material 510 is positioned on the leached PDC cutter 300, and the first insulating material 530 is positioned on the first conducting material 510. The upper plate 552 is moved towards the first insulating material 530 until the downward load 553 is applied onto the leached PDC cutter 300. In an alternative exemplary embodiment, one or more components, such as the first insulating material 530 and the first conducting material 510, are coupled to the upper plate 552 prior to the upper plate 552 being moved towards the base plate 554. Although an Arbor Press 550 is used in the capacitance measuring system 500, other equipment capable of delivering equal and opposite loads to each of the cutting surface 312 and the bottom surface 454 of the leached PDC cutter 300 can be used in other exemplary embodiments.

One end of the first wire 430 is electrically coupled to the positive terminal 418 of the multi-meter 410, while the opposing end of the first wire 430 is electrically coupled to the first conducting material 510, which thereby becomes electrically coupled to the cutting surface 312 of the leached PDC cutter 300. In one exemplary embodiment, a clamp 590 is coupled to the opposing end of the first wire 430 which couples the first wire 430 to the first conducting material 510. One end of the second wire 440 is electrically coupled to the negative terminal 419 of the multi-meter 410, while the opposing end of the second wire 440 is electrically coupled to the second conducting material 520, which thereby becomes electrically coupled to the bottom surface 454 of the leached PDC cutter 300. In one exemplary embodiment, a clamp (not shown), similar to clamp 590, is coupled to the opposing end of the second wire 440, which couples the second wire 440 to the second conducting material 520. Hence, the circuit 505 is completed using the multi-meter 410, the first wire 430, the first conducting material 510, the leached PDC cutter 300, the second conducting material 520, and the second wire 440. The current is able to flow from the positive terminal 418 of the multi-meter 410 to the cutting surface 312 of the leached PDC cutter 300 through the first wire 430 and the first conducting material 510. The current then flows through the leached PDC cutter 300 to the bottom surface 454 of the leached PDC cutter 300. When the multi-meter 410 is turned on, a voltage differential exists between the cutting surface 312 and the bottom surface 454. The current then flows from the bottom surface 454 to the negative terminal 419 of the multi-meter 410 through the second conducting material 520 and the second wire 440. The first insulating material 530 and the second insulating material 540 prevent the current from flowing into the Arbor Press 550. The capacitance measurement of the leached PDC cutter 300 is determined when the value displayed on the display 416 reaches a peak value or remains constant for a period of time.

Figure 6:
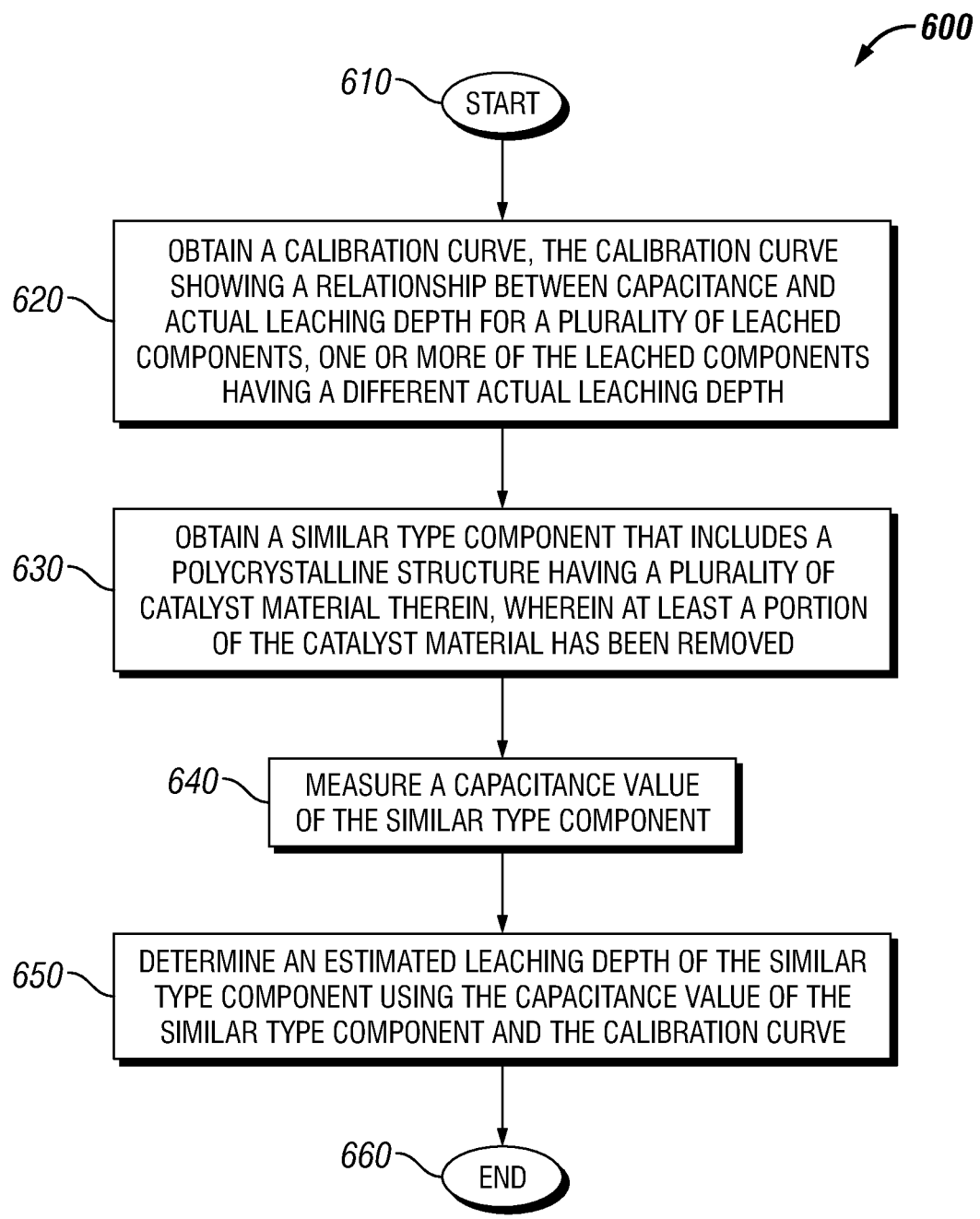
FIG. 6 is a flowchart depicting a non-destructive leaching depth estimation method in accordance with an exemplary embodiment of the present invention.

FIG. 6 is a flowchart depicting a non-destructive leaching depth estimation method 600 in accordance with an exemplary embodiment of the present invention. Although FIG. 6 shows a series of steps depicted in a certain order, the order of one or more steps can be rearranged, combined into fewer steps, and/or separated into more steps than that shown in other exemplary embodiments. Referring to FIG. 6, the non-destructive leaching depth estimation method 600 begins at step 610. Upon starting at step 610, the non-destructive leaching depth estimation method 600 proceeds to step 620. At step 620, a calibration curve is obtained. The calibration curve can be generated from tests or acquired from elsewhere.

Figure 7:
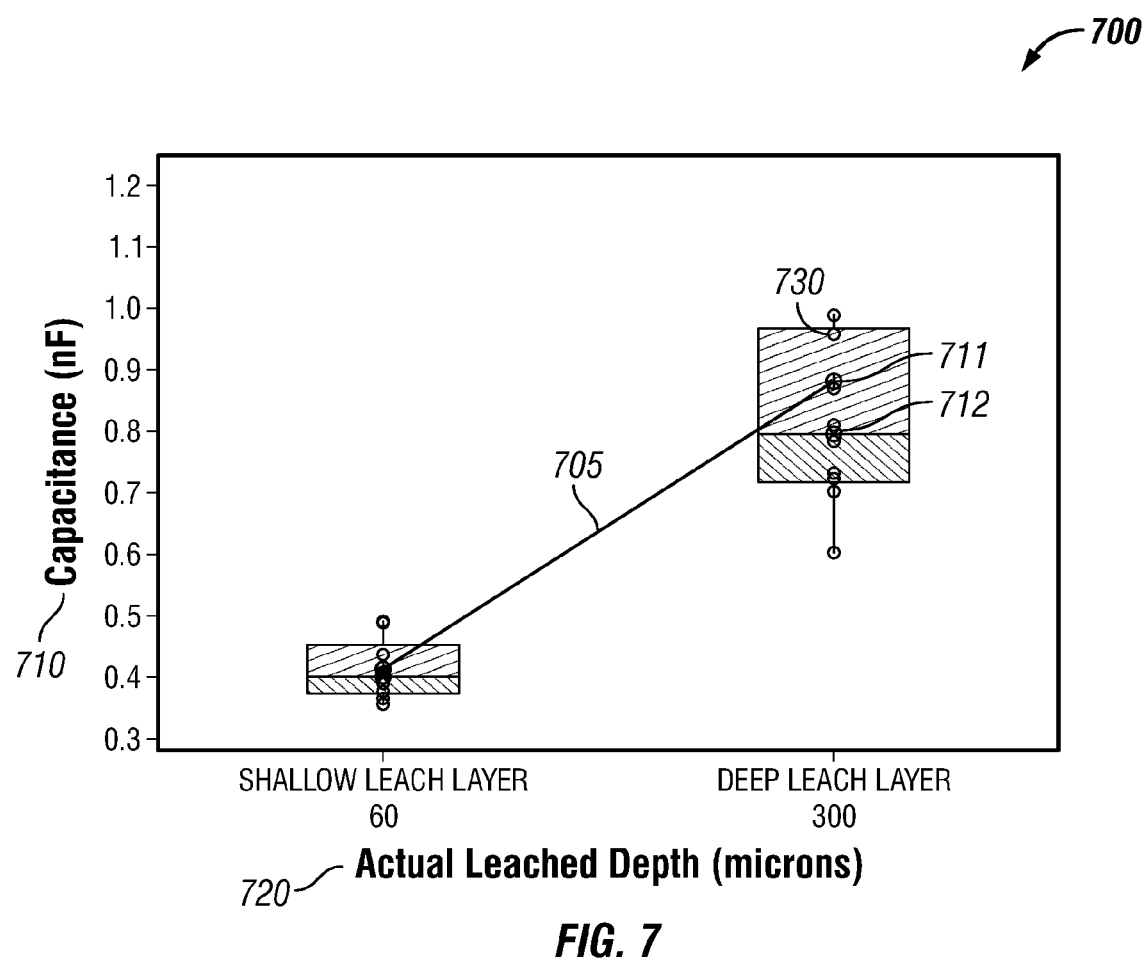
FIG. 7 is a graphical chart depicting a calibration curve that shows a relationship between capacitance and actual leaching depth for a plurality of leached components in accordance with an exemplary embodiment of the present invention.

FIG. 7 is a graphical chart 700 depicting the calibration curve 705 that shows a relationship between capacitance 710 and actual leaching depth 720 for a plurality of leached components 300 (FIG. 3) in accordance with an exemplary embodiment of the present invention. Referring to FIG. 7, one or more of the leached components 300 (FIG. 3) have a different actual leaching depth 720 than at least one other leached component 300 (FIG. 3). The leached component 300 (FIG. 3) is the leached PDC cutter 300 (FIG. 3) according to some exemplary embodiments; however, the leached component 300 can be only the PCD cutting table 310 (FIG. 3) or some other component that has a polycrystalline structure that has had at least some of the catalyst material removed from therein. Alternatively, in certain exemplary embodiments, the leached component 300 can be the chemically cleaned leached PDC cutter mentioned above.

The calibration curve 705 is generated by obtaining two or more leached components 300 (FIG. 3). The calibration curve 705 becomes more precise as more leached components 300 (FIG. 3) are used in generating the calibration curve 705. The capacitance data points 730 are obtained by measuring the capacitance 710 of each leached component 300 (FIG. 3). In certain exemplary embodiments, a plurality of capacitance data points 730 are obtained for each leached component 300 (FIG. 3). For example, the capacitance 710 is measured five times for each leached component 300 (FIG. 3). Obtaining a plurality of capacitance data points 730 for each leached component 300 (FIG. 3) improves the statistical significance of the capacitance data points 730 being collected. According to some exemplary embodiments, the leached component 300 (FIG. 3) is depolarized after each measurement for capacitance 710, before each measurement for capacitance 710, or before and after each measurement for capacitance 710. The leached component 300 is depolarized in one or a combination of different manners, such as grounding the leached component 300 (FIG. 3), wrapping the leached component 300 (FIG. 3) in aluminum foil or similar type material, heat treating the leached component 300 (FIG. 3), dropping the leached component 300 (FIG. 3) in a salt solution, or waiting to discharge the leached component 300 (FIG. 3). The leached component 300 (FIG. 3) is discharged by waiting about twenty-four hours, but the waiting time is greater or less in other exemplary embodiments. Depolarizing an object is known to people having ordinary skill in the art.

Once the capacitance 710 is measured for each leached component 300 (FIG. 3), the actual leaching depth 720 for each leached component 300 (FIG. 3) is determined. In some examples, the actual leaching depth 720 for a leached component 300 (FIG. 3) is determined by cutting the leached component 300 (FIG. 3), polishing the cut edge of the leached component 300 (FIG. 3), and visually measuring the actual leaching depth 720 under a magnifying device (not shown), such as a microscope. Although one method for determining the actual leaching depth 720 is described, other methods known to people having ordinary skill in the art can be used to determine the actual leaching depth 720 without departing from the scope and spirit of the exemplary embodiment. Each capacitance data point 730 is plotted on the graphical chart 700, where the actual leaching depth 720 is plotted versus the capacitance 710 that is measured. Once the capacitance data points 730 are plotted on the graphical chart 700, the calibration curve 705 is determined pursuant to methods known to people having ordinary skill in the art. For example, the calibration curve 705 is generated by using the average capacitance 711 of each leached component 300, the median capacitance 712 of each leached component, or by calculating the best fit curve. The best fit curve can be formed with a ninety-five percent confidence level, but this confidence level can range from about sixty percent to almost about one hundred percent, for example, 99.99 percent. The calibration curve 705 correlates the measured capacitance 710, which can be measured in nanofarads, with the actual leaching depth 720, which can be measured in microns. Although a few methods for generating the calibration curve 705 have been described, other methods, either destructive or non-destructive, can be used to generate the calibration curve 705.

According to FIG. 7, the actual leaching depth 720 is directly related to the capacitance 710. Thus, as the actual leaching depth 720 increases, the capacitance 710 that is measured also increases. Conversely, as the actual leaching depth 720 decreases, the capacitance 710 that is measured also decreases. Additionally, the data scattering, or range of measured capacitance 710, is greater as the actual leaching depth 720 increases. Although FIG. 7 shows a direct relationship between the actual leaching depth 720 and the capacitance 710; in actuality, the relationship between the capacitance 710 and the actual leaching depth 720 is an inverse relationship. The formula to calculate the capacitance 710 is:

$$C = \in_r (A/(4\Pi d))$$

where
C is the capacitance;
A is the area of overlap of the two plates;
$\in_r$ is the relative static permittivity (sometimes called the dielectric constant); and
d is the separation between the plates.

Thus, as "d", or the actual leaching depth 720, increases, the capacitance 710 decreases, and vice versa. The opposite phenomena is occurring in FIG. 7 because the by-product materials 398 (FIG. 3) present with the leached layer 354 (Figure) becomes polarized during the measurements, and thus the relative static permittivity is not constant.

Therefore, in certain exemplary embodiments, the leached layer 354 is treated, such as by chemical treatment, to have at least a portion of the by-product materials 398 (FIG. 3) removed. This treatment is dependent upon the methods and/or chemicals used to leach the PCD cutting table 310 (FIG. 3). This treated leached PDC cutter is used within the capacitance measuring system 400, 500 or within some other capacitance measuring system in lieu of the leached PDC cutter 300 (FIG. 3). The calibration curve that is determined using the treated leached PDC cutters would show the relationship between the actual leaching depth 720 and the capacitance 710 being an inverse relationship. In the methods using the treated leached PDC cutter, which has had at least a portion of the by-product materials 398 (FIG. 3) removed, the de-polarizing step is optional.

Referring back to FIG. 6, the non-destructive leaching depth estimation method 600 proceeds to step 630. At step 630, a similar type component, similar to leached cutter 300, is obtained. However, if the calibration curve was determined using treated leached PDC cutters, the similar type component is a different treated leached PDC cutter where the actual leaching depth is desired to be ascertained. This similar type component includes a polycrystalline structure that has a plurality of catalyst material therein. At least a portion of this catalyst material has been removed. This removed portion has an unknown depth, which is the leaching depth. The non-destructive leaching depth estimation method 600 proceeds to step 640. At step 640, the capacitance of the similar type component is measured. According to some exemplary embodiment, this capacitance is measured using the capacitance measuring system 400 (FIG. 4) or the capacitance measuring system 500 (FIG. 5). The non-destructive leaching depth estimation method 600 proceeds to step 650. At step 650, the estimated leaching depth of the similar type component is determined using the capacitance of the similar type component and the calibration curve 705 (FIG. 7). The estimated leaching depth is an estimation of the actual leaching depth and ranges from about one micron to about fifty microns from the actual leaching depth. The non-destructive leaching depth estimation method 600 proceeds to step 660, where the non-destructive leaching depth estimation method 600 ends.

Figure 8:
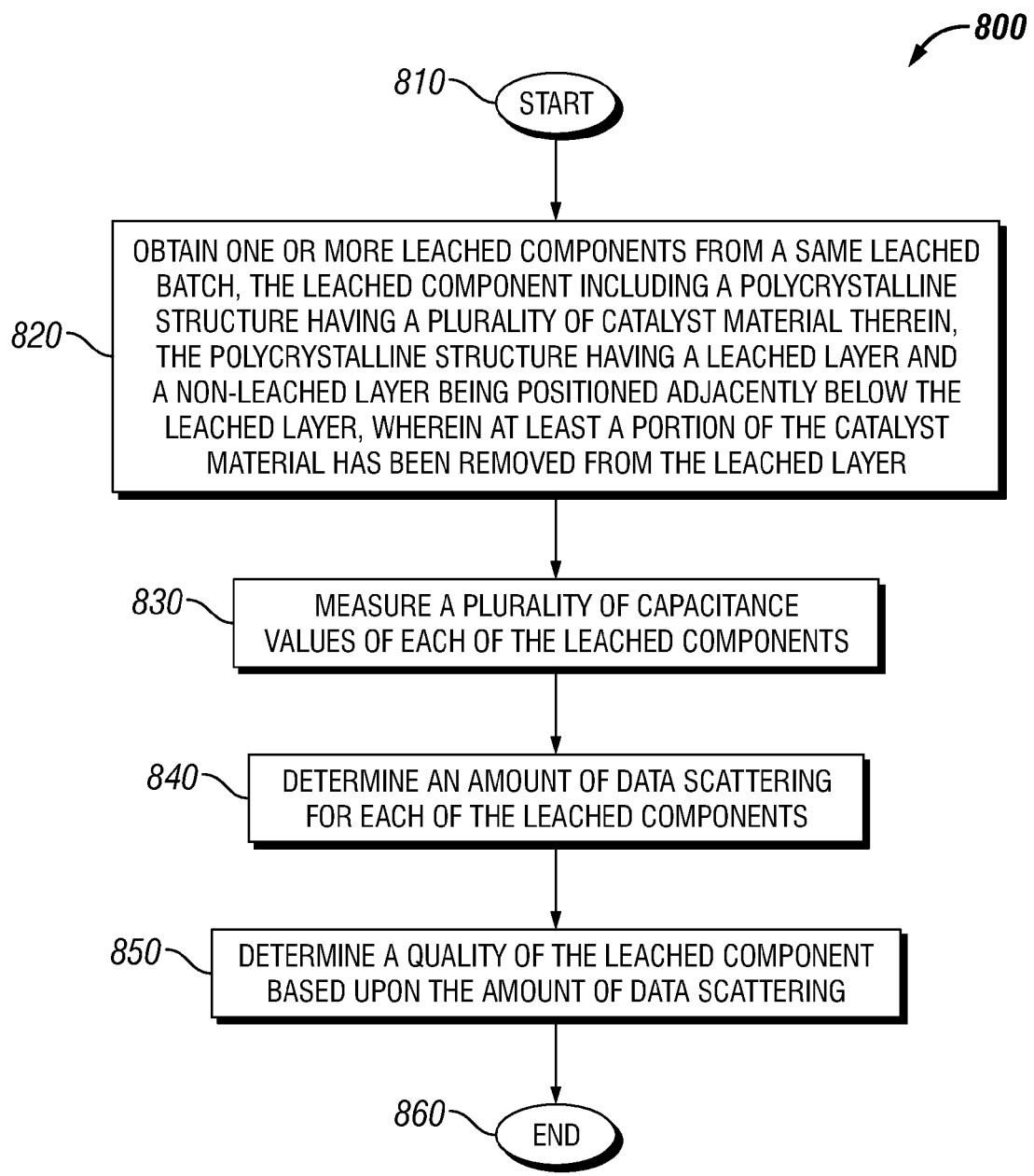
FIG. 8 is a flowchart depicting a microstructural quality determination method in accordance with an exemplary embodiment of the present invention.

FIG. 8 is a flowchart depicting a microstructural quality determination method 800 in accordance with an exemplary embodiment of the present invention. Although FIG. 8 shows a series of steps depicted in a certain order, the order of one or more steps can be rearranged, combined into fewer steps, and/or separated into more steps than that shown in other exemplary embodiments. Referring to FIG. 8, the microstructural quality determination method 800 begins at step 810. Upon starting at step 810, the microstructural quality determination method 800 proceeds to step 820. At step 820, one or more leached components that include a polycrystalline structure is obtained from a same leached batch. The same leached batch is a group of components that were leached in the same leaching process at the same time. The polycrystalline structure includes a leached layer and a non-leached layer being positioned adjacently below the leached layer. The non-leached layer includes a plurality of catalyst material therein, while the leached layer has had at least a portion of the catalyst material removed. The microstructural quality determination method 800 proceeds to step 830. At step 830, a plurality of capacitance values are measured for each of the leached components. The capacitance values are determined using the capacitance measuring system 400 (FIG. 4) or the capacitance measuring system 500 (FIG. 5). The microstructural quality determination method 800 proceeds to step 840. At step 840, an amount of data scattering is determined for each leached component. The amount of data scattering for a leached component is determined by a differential between the highest measured capacitance and the lowest measured capacitance for that leached component and by statistical results of where each measured capacitance lies. The microstructural quality determination method 800 proceeds to step 850. At step 850, a quality of the leached component is determined based upon the amount of data scattering. The quality of the leached component relates to the microstructural quality and/or the leaching quality. The microstructural quality relates to the porosity of the microstructure. The microstructural quality is a good quality when there is low porosity. Conversely, the microstructural quality is a poor quality when there is high porosity. The leaching quality is a good quality when there is less catalyst materials present within the leached layer of the polycrystalline structure. Conversely, the leaching quality is a poor quality when there is more catalyst materials present within the leached layer of the polycrystalline structure. In some exemplary embodiments, the quality of the leached component is considered to be good when the amount of data scattering is determined to be small. Conversely, the quality of the leached component is considered to be poor when the amount of data scattering is determined to be large. The relative terms of small and large are determined when comparing the data scattering of a first leached component to the data scattering of a second leached component that was leached in the same batch as the first leached component.

Figure 9:
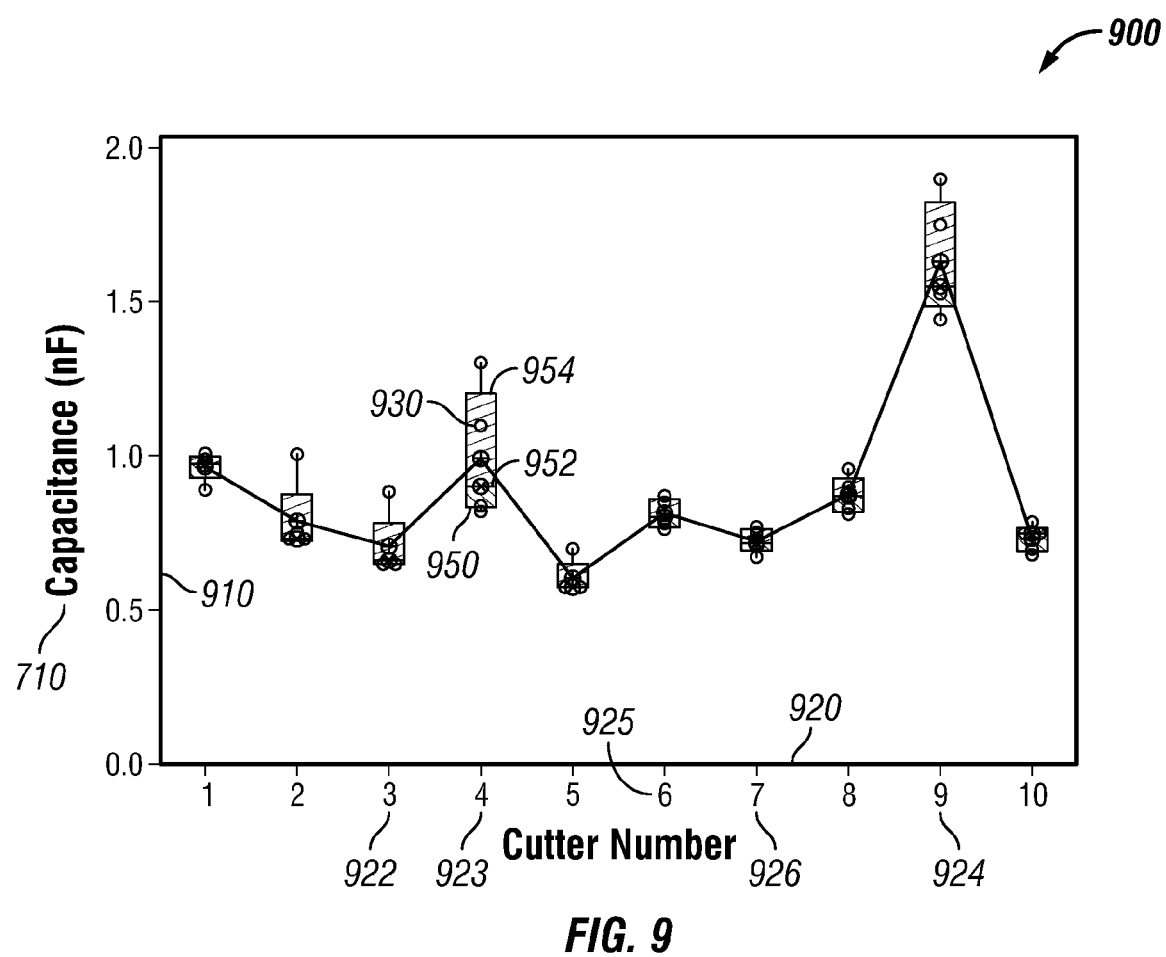
FIG. 9 is a data scattering chart that shows the measured capacitance for a plurality of cutters in accordance with an exemplary embodiment of the present invention.

FIG. 9 is a data scattering chart 900 that shows the measured capacitance 710 for a plurality of leached cutters 922 from a same leaching batch in accordance with an exemplary embodiment of the present invention. Referring to FIG. 9, the data scattering chart 900 includes a cutter number axis 920 and a capacitance axis 910. The cutter number axis 920 includes the number of the cutters 922 tested. The capacitance axis 910 includes values for the measured capacitance 710. A capacitance data point 930 is obtained by measuring the capacitance of the cutter 922, or leached component 922, using the capacitance measuring system 400 (FIG. 4), the capacitance measuring system 500 (FIG. 5), or a similar type system. Each capacitance data point 930 is plotted on the data scattering chart 900. Each leached component 922 has its capacitance measured a plurality of times. In some exemplary embodiments, five capacitance data points 930 are obtained for each leached component 922, however, the number of measurements is greater or fewer in other exemplary embodiments. In some exemplary embodiments, a twenty-five percentile marking 950, a fifty percentile marking 952 (or average), and a seventy-five percentile marking 954 is shown in the chart 900 for each leached component 922. The area between the twenty-five percentile marking 950 and the seventy-five percentile marking 954 is shaded. The amount of data scattering is ascertained using this data scattering chart 900 and can be one or more of a differential between the highest and lowest capacitance measurements 710 for each leached component 922, a range between the twenty-five percentile marking 950 and the seventy-five percentile marking 954, or some similar observation made from the data scattering chart 900.

According to FIG. 9, cutter number 4 923 and cutter number 9 924 have a larger data scattering than for example cutter number 6 925 or cutter number 7 926. Hence, cutter number 4 923 and cutter number 9 924 have a poor leaching quality and/or a poor microstructural quality within the polycrystalline structure. The increase in amount of catalyst material within the polycrystalline structure causes this data scattering.

Figure 10:
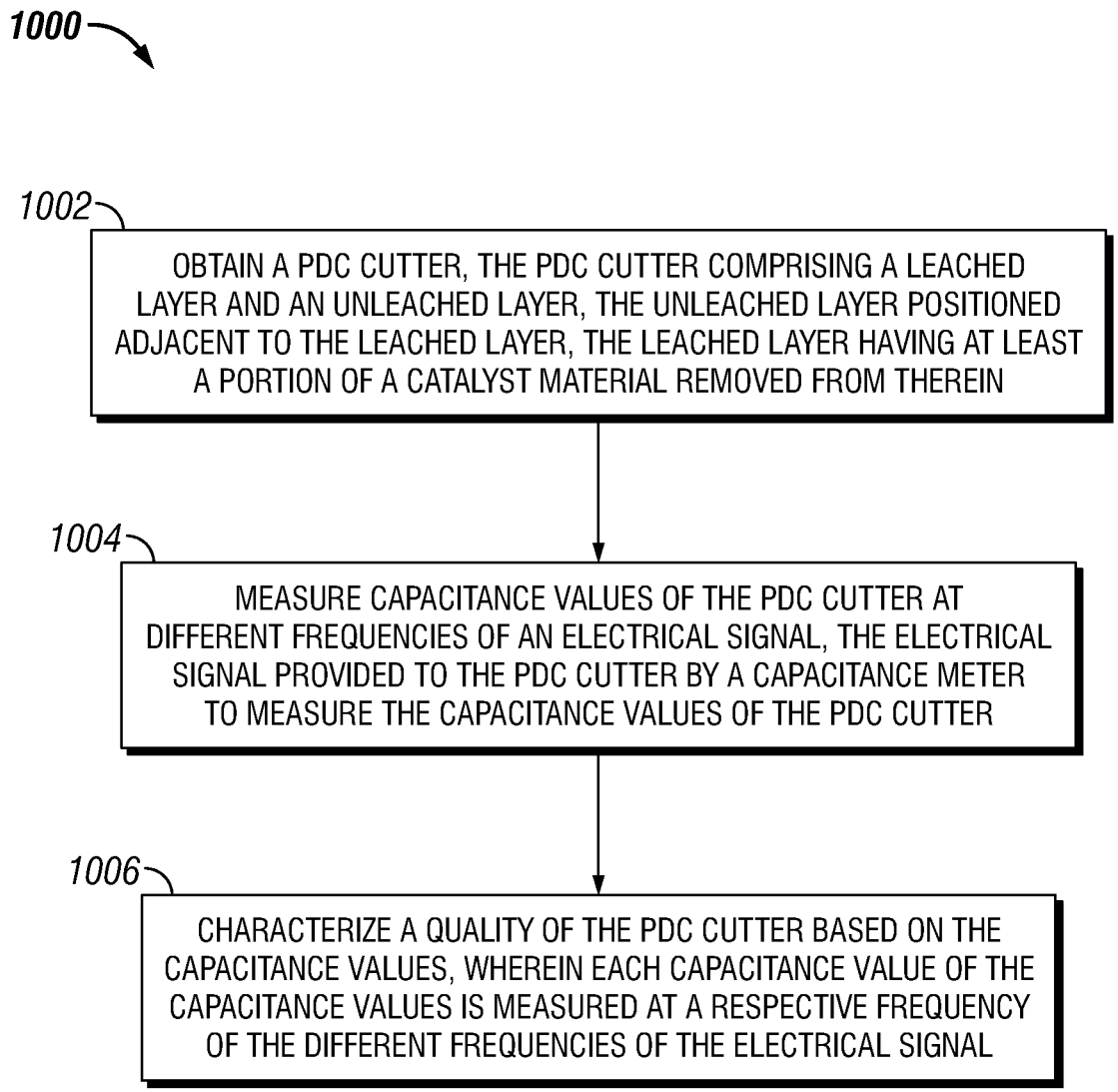
FIG. 10 is a flowchart depicting a non-destructive method of characterizing a quality of a PDC cutter in accordance with an exemplary embodiment of the present invention.

FIG. 10 is a flowchart depicting a non-destructive method 1000 of characterizing a quality of a PDC cutter in accordance with an exemplary embodiment of the present invention. The method 1000 includes obtaining a PDC cutter at step 1002. For example, the PDC cutter 300 of FIG. 3 may be obtained for characterizing the quality of the PDC cutter 300. The PDC cutter obtained at step 1002 includes a leached layer and an unleached layer, and the unleached layer is positioned adjacent to the leached layer. To illustrate, the PDC cutter 300 has the leached layer 354 and the unleached layer 356 adjacent to the leached layer 354. As described with respect to the PDC cutter 300 of FIG. 3, the leached layer of the PDC cutter has at least a portion of a catalyst material removed from within the leached layer.

At step 1004, the method 1000 includes measuring capacitance values of the PDC cutter at multiple frequencies of an electrical signal. The electrical signal is provided to the PDC cutter by a capacitance measuring device to measure the capacitance values of the PDC cutter. The electrical signal may result in a voltage differential across surfaces of the PDC cutter due to capacitive characteristics of the portions of the PDC cutter, such as the leached layer. For example, the capacitance measuring device of FIGS. 4 and 5 may be used to measure the capacitance values of the PDC cutter (e.g., the PDC cutter 300 of FIG. 3) at multiple frequencies of an electrical signal. To illustrate, the capacitance measuring device 410 may provide an electrical signal to the PDC cutter 300 to measure capacitance values of the PDC cutter 300 at different frequencies of the electrical signal. For example, the capacitance measuring device 410 may provide the electrical signal to the PDC cutter through the first wire 430.

In some exemplary embodiments, the capacitance measuring device 410 automatically changes the frequency of the electrical signal and measures the capacitance value of the PDC cutter after every change in the frequency. Alternatively, the frequency of the electrical signal provided to the PDC cutter may be changed manually and a capacitance value of the PDC cutter may be measured by the capacitance measuring device 400 after each manual change in frequency. In some exemplary embodiments, the frequency of the electrical signal may be changed within a range of approximately 0 Hertz to approximately 10 Megahertz at a particular frequency increment or decrement. In some alternative embodiments, the frequency of the electrical signal may be changed within other ranges of frequency. To measure the capacitance of the PDC cutter at multiple frequencies of the electrical signal, the capacitance measuring device 400 may automatically sweep through a range of frequencies of the electrical signal at a particular frequency increment and may measure the capacitance of the PDC cutter after each increment in the frequency.

At step 1006, the method 1000 includes characterizing a quality of the PDC cutter based on the capacitance values. As described above, each capacitance value of the capacitance values is measured at a respective frequency of the multiple frequencies of the electrical signal. In some exemplary embodiments, characterizing the quality of the PDC cutter includes determining a lowest capacitance value from among the capacitance values. To illustrate, after multiple capacitance values of the PDC cutter (e.g., the PDC cutter 300) are measured at the multiple frequencies within a range of frequencies, the lowest capacitance value from among the multiple capacitance values is identified. For example, the lowest capacitance values may be 70 picofarad (pF) for a particular PDC cutter.

In some exemplary embodiments, characterizing the quality of the PDC cutter further includes determining, using capacitance to leaching depth mapping information, a leaching depth value that corresponds to the lowest capacitance value. The leaching depth value is an estimate of the actual depth of the leached layer of the PDC cutter. To illustrate with respect to the PDC cutter 300 of FIG. 3, the leaching depth value is consider to be an estimate of the depth of the leached layer 354. The capacitance to leaching depth mapping information may be obtained from a calibration curve (e.g., a calibration curve shown in FIG. 12). In some example embodiments, the method 1000 may also include obtaining (e.g., by generating) a calibration curve that may be used for mapping the lowest capacitance value to a leaching depth value. A method of generating a calibration curve is described below with respect to FIG. 13. In some alternative embodiments, the capacitance to leaching depth mapping information may be in other forms, such as a formula, that may be used to calculate the leaching depth value using the lowest capacitance value as an input.

As described above with respect to FIG. 7, in some exemplary embodiments, the method 1000 may include cleaning the leached layer to remove one or more by-product materials deposited within the leached layer during a leaching process that removes at least a portion of the catalyst material to form the leached layer. For example, the leached layer of the PDC cutter obtained at step 1002 may have been cleaned prior to measuring capacitance values of the PDC cutter at step 1004.

Although the method 1000 is described with respect to a PDC cutter, such as the PDC cutter 300 of FIG. 3, the method 1000 is generally applicable to a leached component that may be obtained at step 1002. To illustrate, a leached component (i.e., the PDC cutter or another type of leached component) may be obtained at step 1002. In general, the leached component includes a polycrystalline structure that includes a leached layer and an unleached layer, where the leached layer has at least a portion of a catalyst material removed from therein. At step 1004, the method 1000 may include measuring capacitance values of the leached component at multiple frequencies of the electrical signal. The electrical signal is provided to the leached component by a capacitance measuring device to measure capacitance of the leached component in a similar manner described above with respect to the PDC cutter. At step 1006, the method includes characterizing a quality of the leached component based on the capacitance values. As described above with respect to the PDC cutter and step 1006 of the method 1000, each capacitance value of the capacitance values of the leached component is measured at a respective frequency of the multiple frequencies of the electrical signal. Characterizing the quality of the leached component includes determining a lowest capacitance value from among the capacitance values measured in a similar manner described above with respect to the PDC cutter and step 1004.

Although the method 1000 is described with respect to capacitance measurement and capacitance values, in alternative embodiments, the method 1000 may instead be implemented based on impedance measurement and impedance values (in units of ohms) in a manner similar to the steps described above without departing from the scope of this disclosure. For example, an impedance measuring device may be used to measure impedance values of the PDC cutter and the quality of the PDC cutter may be characterized using the impedance values, for example, based on impedance to leaching depth mapping information.

Figure 11:
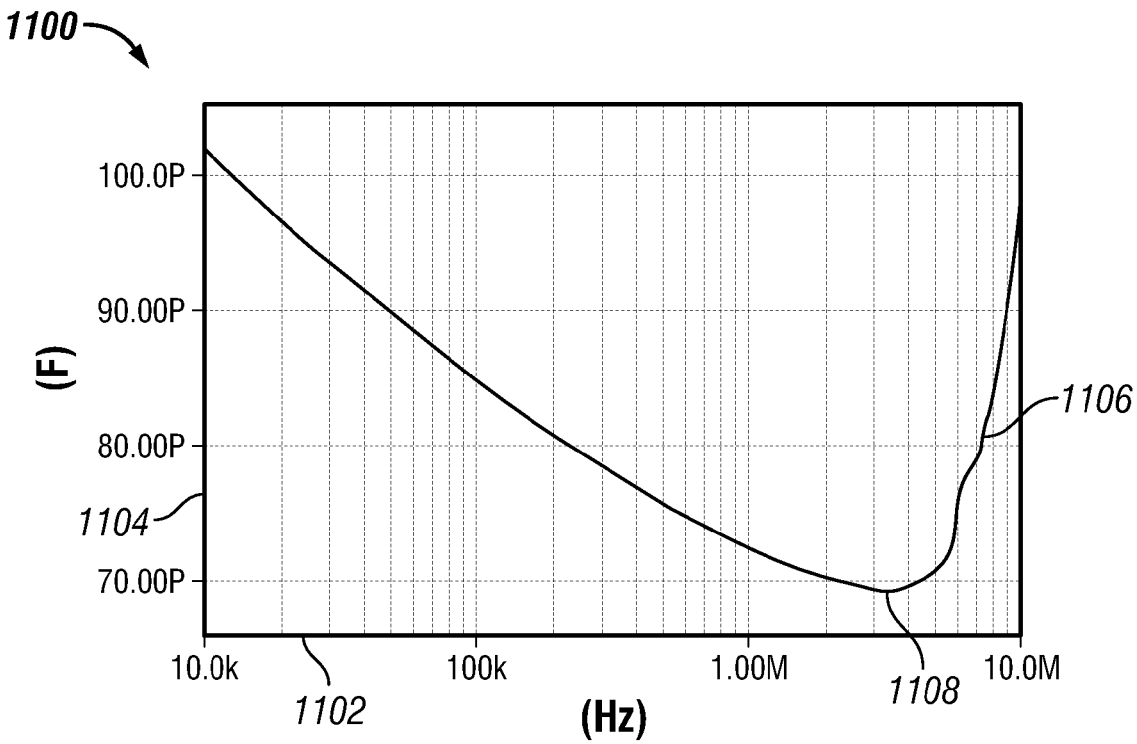
FIG. 11 is a graph depicting capacitance values of a PDC cutter measured at multiple frequencies in accordance with an exemplary embodiment of the present invention.

FIG. 11 is a graph 1100 depicting capacitance values of a PDC cutter measured at multiple frequencies in accordance with an exemplary embodiment of the present invention. For example, the PDC cutter may be the PDC cutter 300 of FIG. 3. In the graph 1100, frequency values (in hertz) are shown on the x-axis 1002, and capacitance values (in picofarads) are shown on the y-axis 1004. The curve 1106 is a plot of measured capacitance values of the PDC cutter and corresponding frequency values of an electrical signal used in measuring the capacitance values of the PDC cutter. As described above with respect to the method 1000 of FIG. 10, a capacitance measuring device, such as the capacitance measuring device 410 of FIG. 4, may be used to measure capacitance values of the PDC cutter at multiple frequencies. For example, a frequency range of 10 kilohertz to 10 Megahertz is shown in the graph 1100. In some alternative embodiments, the frequency range may be narrower or wider than shown in the graph 1100.

As described above with respect to the method 1000 of FIG. 10, characterizing the quality of the PDC cutter includes determining the lowest capacitance value from among the capacitance values measured by the capacitance measuring device. To illustrate, the lowest capacitance value in the graph 1100 is at data point 1108, which is approximately 70 picofarads. The lowest capacitance value may be more precisely determined by displaying higher resolution intervals of the capacitance values on the y-axis 1104. As described above with respect to the method 1000 of FIG. 10, the lowest capacitance value determined from the graph 1100 may be used to determine a leaching depth value, which is an estimate of an actual depth of a leached layer of the PDC cutter, such as the leached layer 354 of the PDC cutter 300 of FIG. 3.

In some example embodiments, the graph 1100 may be generated by the capacitance measuring device, such as the capacitance measuring device 410 of FIG. 4. Alternatively, the graph 1100 may be generated based on measurement data (i.e., capacitance and frequency values) obtained from the capacitance measuring device.

Although the graph 1100 illustrates capacitance values of a PDC cutter measured at multiple frequencies, in some alternative embodiments, the graph 1100 may illustrate impedance values of the PDC cutter measured at multiple frequencies and may be generated and used a manner similar to the capacitance values described above without departing from the scope of this disclosure.

Figure 12:
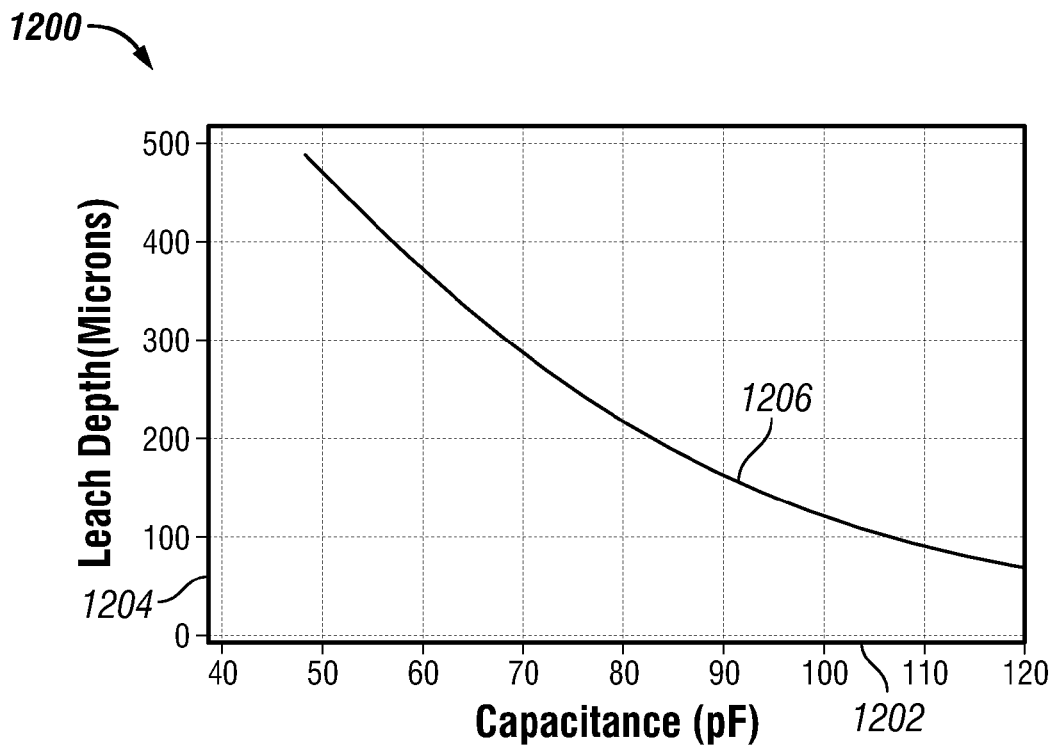
FIG. 12 is a graph depicting a calibration curve that shows a relationship between capacitance values and actual leaching depth values for estimating an actual depth of a PDC cutter in accordance with an exemplary embodiment of the present invention.

FIG. 12 illustrates a graph 1200 depicting a calibration curve 1206 that shows a relationship between capacitance values and leaching depth values for estimating an actual depth of a PDC cutter in accordance with an exemplary embodiment of the present invention. In the graph 1200, capacitance values (in picofarads) are shown on the x-axis 1202, and leach depth values (in microns) are shown on the y-axis 1204. The generation of the calibration curve 1206 is described below in more detail with respect to FIG. 13.

In some exemplary embodiments, the graph 1200 may be used in the method 1000 of FIG. 10 to characterize a quality of PDC cutters or other leached components. To illustrate, after capacitance values of the PDC cutter (e.g., the PDC cutter 300) are measured at the multiple frequencies, the lowest capacitance value from among the multiple capacitance values is determined as described with respect to FIGS. 10 and 11.

Once the lowest capacitance value is determined, the calibration curve 1206 may be used to map the lowest capacitance value from the x-axis 1202 to a leaching depth value on the y-axis 1204. For example, if the lowest capacitance value is determined to be approximately 70 picofarads, the leaching depth value may be determined to be approximately 280 microns based on the calibration curve 1206. In some exemplary embodiments, the leaching depth value determined using the graph 1200 is an estimate of the actual depth of the leached layer of the PDC cutter. To illustrate with respect to the PDC cutter 300 of FIG. 3, the leaching depth value determined using the calibration curve 1206 is an estimate of the actual depth of the leached layer 354 of the PDC cutter 300.

As illustrated in FIG. 12, the graph 1200 may be used to map capacitance values ranging from approximately 48 picofarads to 120 picofarads to corresponding leaching depth values ranging from approximately 70 microns to approximately 490 microns. Although particular ranges of capacitance and leaching depth values are shown in FIG. 12, in alternative embodiments, the graph 1200 may have wider or narrower ranges of capacitance and leaching depth values that may be used for reliably mapping capacitance values to leaching depth values as described above.

Although FIG. 12 illustrates the calibration curve 1206 that shows a relationship between capacitance values and leaching depth values for estimating an actual depth of a PDC cutter, in some alternative embodiments, a calibration curve that shows a relationship between impedance values and leaching depth values may be generated and used for estimating an actual depth of a PDC cutter. A calibration curve that shows a relationship between impedance values and leaching depth values may be generated and used in a manner similar to the generation and use of the calibration curve 1206.

Figure 13:
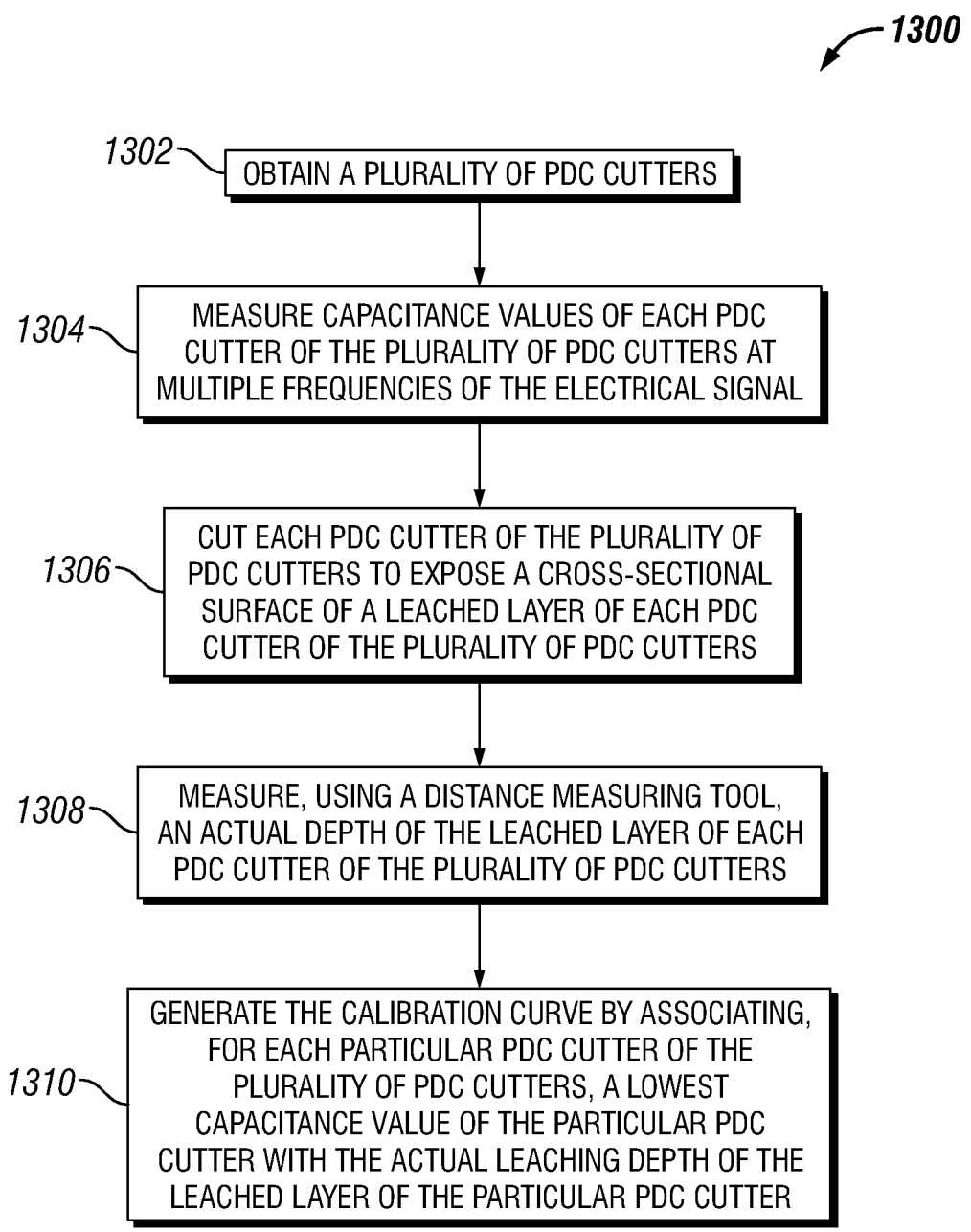
FIG. 13 is a flowchart depicting a method of generating a calibration curve for use in characterizing a quality of a PDC cutter in accordance with an exemplary embodiment of the present invention.

FIG. 13 is a flowchart depicting a method 1300 of generating a calibration curve for use in characterizing a quality of a PDC cutter in accordance with an exemplary embodiment of the present invention. For example, the method 1300 may be used to generate the graph 1200 of FIG. 12. At step 1302, the method 1300 includes obtaining a plurality of PDC cutters. The plurality of PDC cutters are obtained for the purpose of generating a calibration curve (e.g., the calibration curve 1206 of FIG. 12) or other capacitance to leaching depth mapping information (e.g., an equation or a mapping table) for use in estimating an actual depth of a leached layer of the same type PDC cutter using a method such as the method 1000 of FIG. 10. For example, the method 1300 may include obtaining a plurality of the PDC cutters 300 of FIG. 3.

At step 1304, the method 1300 includes measuring capacitance values of each PDC cutter of the plurality of PDC cutters at multiple frequencies of the electrical signal. For example, the capacitance values of each PDC cutter of the plurality of PDC cutters may be measured at multiple frequencies of an electrical signal in a manner described above with respect to FIG. 10. As described above, the electrical signal is provided to each PDC cutter individually by a capacitance measuring device, such as the capacitance measuring device 400 of FIGS. 4 and 5. In some exemplary embodiments, the leached layer of each PDC cutter may be cleaned to remove one or more by-product materials deposited within the leached layer during a leaching process that removes at least a portion of the catalyst material to form the leached layer. For example, the method 1300 may include cleaning the leached layer of each PDC cutter to remove the one or more by-product materials. Alternatively, each PDC cutter obtained at step 1302 may have a leached layer that has been cleaned remove one or more by-product materials.

At step 1306, the method includes cutting each PDC cutter of the plurality of PDC cutters to expose a cross-sectional surface of a leached layer of each PDC cutter of the plurality of PDC cutters. As an illustrative example, a cross-section of the PDC cutter 300 is shown in FIG. 3, which illustrates a cross-sectional surface of the leached layer 354. At step 1308, the method 1300 includes measuring an actual depth of the leached layer of each PDC cutter of the plurality of PDC cutters. The actual depth may be measured using a distance measuring tool known to those of ordinary skill in the art with the benefit of this disclosure. A microscope or other similar magnifying device may be used to aid with the measuring of the actual depth of the leached layer. In some exemplary embodiments, the actual depth of the leached layer of each PDC cutter of the plurality of PDC cutters may be measured in a similar manner described with respect to FIG. 7. In some exemplary embodiments, the method 1300 may also include polishing the cross-sectional surface of the leached layer of each PDC cutter of the plurality of PDC cutters.

At step 1310, the method 1300 includes generating the calibration curve by associating, for each particular PDC cutter of the plurality of PDC cutters, a lowest capacitance value of the capacitance values of the particular PDC cutter with the actual leaching depth of the leached layer of the particular PDC cutter. To illustrate, once the capacitance values of a particular PDC cutter of the plurality of PDC cutters are measured at multiple frequencies at step 1304, the lowest capacitance value among the capacitance values may be determined as described with respect to FIGS. 10 and 11.

After the lowest capacitance value is determined for a particular PDC cutter and after the actual leaching depth of the leached layer of the PDC cutter is measured at step 1308, the lowest capacitance value and the actual leeching depth value may be plotted as a data point in a graph such as the graph 1200 of FIG. 12. After data points are plotted for the plurality of the cutters, a best fit curve (i.e., a calibration curve such as the calibration curve 1206 of FIG. 12) may be generated in a manner know to those of ordinary skill in the art with the benefit of this disclosure. In some exemplary embodiments, instead of or in addition to the calibration curve, another format of the capacitance to leaching depth mapping information (e.g., an equation or a mapping table) may be generated based on the relationship between the lowest capacitance values of the plurality of PDC cutters and the actual leaching depths of the leaching layers of the plurality of PDC cutters.

The calibration curve and other formats of the capacitance to leaching depth mapping information generated by the method 1300 may be used in a similar manner described above with respect to FIGS. 6, 10, and 12 for the purpose of estimating a leaching depth of the leaching layer of a PDC cutter that is of the same type as the plurality of the PDC cutters used in the generation of the calibration curve and other formats of the capacitance to leaching depth mapping information.

Although the method 1300 is described above with respect to capacitance values, in alternative embodiments, the method 1300 may be implemented based on impedance values of the PDC cutter in a manner similar to the steps described above. For example, a calibration curve showing a relationship between impedance values and leaching depth values of the PDC cutters may be generated, and the quality of the PDC cutter may be characterized based on such calibration curve.

Figure 14:
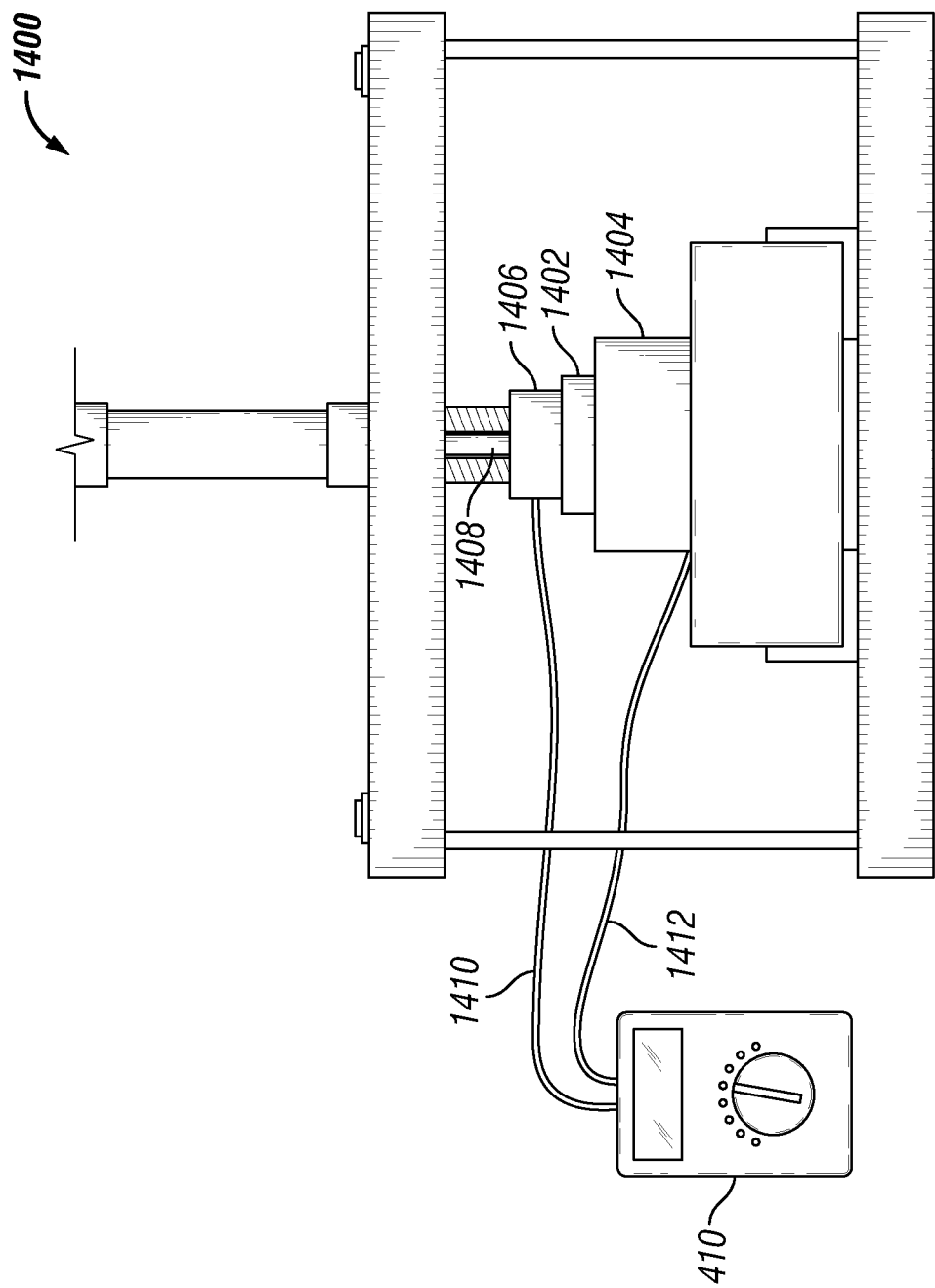
FIG. 14 illustrates a capacitance measuring system for characterizing a quality of a PDC cutter in accordance to an exemplary embodiment of the present invention.

FIG. 14 illustrates a capacitance measuring system 1400 for characterizing a quality of a PDC cutter in accordance to an exemplary embodiment of the present invention. In some exemplary embodiments, the system 1400 may be used to implement the method 1000 of FIG. 10 and the method 1300 of FIG. 13. The system 1400 includes the capacitance measuring device 410, also shown in FIGS. 4 and 5. In some exemplary embodiments, the capacitance measuring device 410 may be Instek LCR-8110G LCR meter. The capacitance measuring device 410 has the terminal 418 and the terminal 419 as shown in FIG. 4. In some example embodiments, the system 1400 includes a first cap 1402 and a second cap 1404 that are electrically conductive. The system 1400 also includes a PDC cutter, such as the PDC cutter 300 shown in FIGS. 3 and 5. In the exemplary system 1400 shown in FIG. 14, the PDC cutter is blocked from view by the first cap 1402 and the second cap 1404. As described above, for example with respect to FIG. 3, the PDC cutter has a leached layer and an unleached layer that is adjacent to the leached layer. The leached layer has at least a portion of a catalyst material removed from therein using a leaching process.

In some exemplary embodiments, the PDC cutter may have been cleaned to remove one or more by-product materials deposited within the leached layer during a leaching process that removes at least a portion of the catalyst material to form the leached layer. The system 1400 also includes a first wire 1410 electrically coupling the first terminal of the capacitance measuring device 410 to a first surface of the PDC cutter. For example, the first surface of the PDC cutter may be the cutting surface 312 of the PDC cutter 300 shown in FIGS. 3 and 5.

The system 1400 further includes a second wire 1412 electrically coupling the second terminal of the capacitance measuring device 410 to a second surface of the PDC cutter. For example, the second surface of the PDC cutter may be the bottom surface 454 of the PDC cutter 300 shown in FIG. 4. As illustrated in FIGS. 3 and 4, the first (cutting) surface 312 and the second (bottom) surface 454 of the PDC cutter 300 are on opposite sides of the leached layer 354, and the first surface 312 is a surface of the leached layer 354. The capacitance measuring device 410 provides an electrical signal to the PDC cutter, such as the PDC cutter 300, to measure capacitance values of the PDC cutter. As described above, the capacitance measuring device 410 measures the capacitance values of the PDC cutter at multiple frequencies of the electrical signal. To illustrate, the capacitance measuring device 410 can measure the capacitance values of a PDC cutter at multiple frequencies of the electrical signal in the method 1000 as well as the method 1300.

Figure 16:
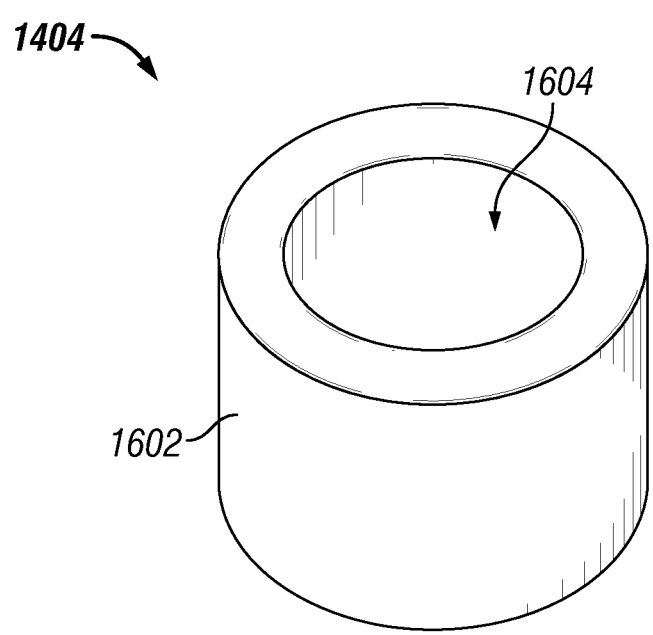
FIG. 16 illustrates another cap used in conjunction with the cap of FIG. 15 in accordance to an exemplary embodiment of the present invention.

In some example embodiments, the first cap 1402 is coupled to the first surface of the PDC cutter, such as the cutting surface 312 of the PDC cutter 300. Similarly, the second cap 1404 may be coupled to the second surface of the PDC cutter, such as the bottom surface 454 of the PDC cutter 300. To illustrate, a portion of the PDC cutter including the second surface of the PDC may be positioned in a cavity of the second cap 1404. The cavity of the second cap 1404 is illustrated in FIG. 16. For example, at least a portion of the substrate 350 of the PDC cutter 300 may be positioned in cavity of the second cap 1404.

In some example embodiments, the first wire 1410 is electrically coupled to the first cap 1402, and the second wire 1412 is electrically coupled to the second cap 1404. For example, the system 1400 may include an electrically conductive terminal 1406 attached to a piston 1408, which may be vertically moveable. As illustrated in FIG. 14, the first wire 1410 is physically attached to the terminal 1406, and the terminal 1406 may be lowered to the position shown in FIG. 14 and in contact with the cap 1402. The second wire 1412 may be directly attached to the second cap 1404 as illustrated in FIG. 14.

During operation, a PDC cutter, such as the PDC cutter 300 of FIG. 3, is positioned in the cavity of the second cap 1404 such that the second surface and/or another part of the substrate of the PDC cutter (e.g., the bottom surface 454 or another part of the substrate 350 of the PDC cutter 300) is in physical contact with a conductive surface of the second cap 1404. The first surface, such as the cutting surface 312 or another part of the leached layer 354, does not come in physical contact with a conductive surface of the second cap 1404. After the PDC cutter is positioned in the cavity of the second cap 1404, the first cap 1402 is positioned on the PDC cutter such that a conductive surface of the first cap 1402 is in physical contact with the first surface of the PDC cutter, such as the cutting surface 312 of the PDC cutter 300.

The electrically conductive terminal 1406 may then be lowered by the piston 1408 such that the electrically conductive terminal 1406 comes in physical contact with the first cap 1402. Alternatively, the first cap 1402 may first attached to the electrically conductive terminal 1406 and lowered until the conductive surface of the first cap 1402 comes in physical contact with the first surface of the PDC cutter, such the cutting surface 312 of the PDC cutter 300. After a complete electrical path is established as described above, the capacitance measuring device 410 may start measuring the capacitances values of the PDC cutter at multiple frequencies of electrical signal provided by the capacitance measuring device 410 to the PDC cutter via one of the wires 1410, 1412. As described above, the multiple frequencies of the electrical signal may range between approximately 0 Hertz and approximately 10 Megahertz or other suitable frequency values depending on, for example, the type of PDC cutter.

Although FIG. 14 described as illustrating the capacitance measuring system 1400, in some alternative embodiments, the system 1400 may be used as an impedance measuring system in a similar manner described above without departing from the scope of this disclosure.

Figure 15:
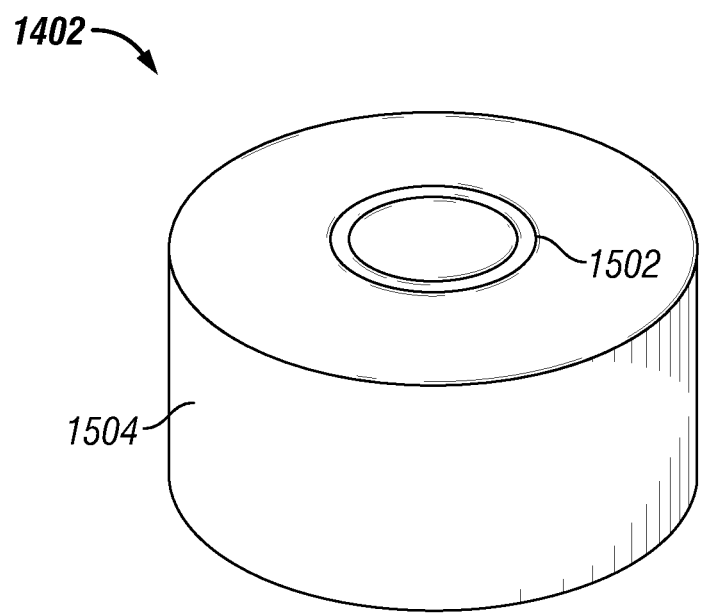
FIG. 15 illustrates a cap used in the capacitance measuring system of FIG. 14 in accordance to an exemplary embodiment of the present invention.

FIG. 15 illustrates the first cap 1402 used in the capacitance measuring system 1400 of FIG. 14 in accordance to an exemplary embodiment of the present invention. As illustrated in FIG. 15, the first cap 1402 has an electrically conductive surface 1502 and an electrically insulated surface 1504. As described above with respect to FIG. 14, the electrically conductive surface 1502 is designed to come in contact with the first surface of the PDC cutter, such as the cutting surface 312 of the PDC cutter 300. The electrically insulated surface 1504 is designed to electrically isolate the electrically conductive surface 1502 and any other electrically conductive part of the first cap 1402 from coming in contact with the PDC cutter as well as the second cap 1404.

As illustrated in FIG. 15, the conductive surface 1502 may have ring shape having particular thickness. For example, the conductive surface 1502 may be shaped and sized such that the conductive surface 1502 is physical contact with the cutting surface 312 of the PDC cutter 300 proximal to the outer perimeter of the cutting surface 312. In alternative embodiments, the conductive surface 1502 may be shaped and sized to come in contact with other parts of the conductive surface 1502 including the entire cutting surface 312. The electrically conductive surface 1502 and other parts of the first cap 1402 may be made from copper or another electrically conductive material. The electrically insulated surface 1504 may be made from plastic or another electrically non-conductive material. Although the first cap 1402 is shown as having a cylindrical shape, in alternative embodiments, the first cap 1402 may have other shapes without departing from the scope of this disclosure. In some alternative embodiments, the first cap 1402 may be used in the system 1400 for measuring impedance of a PDC cutter.

FIG. 16 illustrates the second cap 1404 used in conjunction with the first cap 1402 in the capacitance measuring system 1500 of FIG. 14 in accordance to an exemplary embodiment of the present invention. As illustrated in FIG. 16, the second cap 1404 has a cavity 1604 bound by a wall 1602 including a bottom wall (not shown) of the second cap 1404. As described above, the PDC cutter 300 may be positioned within the cavity 1604 such that the bottom surface 454 of the PDC cutter 300 come in contact with the surface of the second cap 1404. The second cap 1404 may be made from copper or another electrically conductive material. Although the second cap 1404 is shown as having a cylindrical shape, in alternative embodiments, the second cap 1404 may have other shapes without departing from the scope of this disclosure. In some alternative embodiments, the second cap 1404 may be used in the system 1400 for measuring impedance of a PDC cutter.

There are several benefits for non-destructively determining the leaching depth in an ultra-hard polycrystalline structure and/or characterizing at least a portion of the ultra-hard polycrystalline structure. For example, capacitance measurements can be made on all PDC cutters that are to be mounted and used in a tool, such as a drill bit, thereby being able to estimate the leaching depth in the ultra-hard polycrystalline structure included in the PDC cutter and/or characterizing at least a portion of the ultra-hard polycrystalline structure, such as the quality of the leaching and/or the quality of the microstructure. Hence, only certain PDC cutters are chosen to be mounted to the drill bit or other downhole tool. In another example, when a quantity of PDC cutters being leached within the same leaching batch are provided, such as one thousand PDC cutters, the capacitance of the PDC cutters are measured pursuant to the descriptions provided above. The PDC cutters that meet a desired quality and/or leaching depth are kept while the remaining PDC cutters that do not meet the desired leaching depth and/or quality are returned. Thus, in one exemplary embodiment, although one thousand PDC cutters being leached from the same batch are provided, two hundred PDC cutters, or twenty percent, may be retained while the remaining are returned. Thus, only the higher quality and/or the proper leaching depth PDC cutters are paid for and retained, which results in the PDC cutters performing better during their application.

Although each exemplary embodiment has been described in detail, it is to be construed that any features and modifications that are applicable to one embodiment are also applicable to the other embodiments. Furthermore, although the invention has been described with reference to specific embodiments, these descriptions are not meant to be construed in a limiting sense. Various modifications of the disclosed embodiments, as well as alternative embodiments of the invention will become apparent to persons of ordinary skill in the art upon reference to the description of the exemplary embodiments. It should be appreciated by those of ordinary skill in the art that the conception and the specific embodiments disclosed may be readily utilized as a basis for modifying or designing other structures or methods for carrying out the same purposes of the invention. It should also be realized by those of ordinary skill in the art that such equivalent constructions do not depart from the spirit and scope of the invention as set forth in the appended claims. It is therefore, contemplated that the claims will cover any such modifications or embodiments that fall within the scope of the invention.

What is claimed is:

1. A method of characterizing a quality of a polycrystalline diamond compact cutter, the method comprising:
    obtaining the polycrystalline diamond compact cutter, the polycrystalline diamond compact cutter comprising a leached layer and an unleached layer, the unleached layer positioned adjacent to the leached layer, the leached layer having at least a portion of a catalyst material removed from therein;
    measuring capacitance values of the polycrystalline diamond compact cutter at multiple frequencies of an electrical signal, the electrical signal provided to the polycrystalline diamond compact cutter by a capacitance meter,
    wherein each capacitance value of the capacitance values is measured at a respective frequency of the multiple frequencies of the electrical signal;
    selecting a lowest capacitance value from among the measured capacitance values; and
    determining, using capacitance to leaching depth mapping information, a leaching depth value that corresponds to the selected lowest capacitance value,
    wherein the leaching depth value is an estimate of an actual depth of the leached layer of the polycrystalline diamond compact cutter.

2. The method of claim 1, further comprising:
    obtaining a plurality of sample polycrystalline diamond compact cutters;
    measuring capacitance values of each sample cutter at the multiple frequencies of the electrical signal;
    cutting each sample cutter o expose a cross-sectional surface of a leached layer of each sample cutter;
    measuring, using a distance measuring tool, an actual depth of the leached layer of each sample cutter; and
    generating the leaching depth mapping information by associating, for each particular sample cutter, a lowest capacitance value of the capacitance values of the particular sample cutter with the actual leaching depth of the leached layer of the particular sample cutter.

3. The method of claim 2, wherein obtaining the leaching depth mapping information further comprises polishing the cross-sectional surface of the leached layer of each sample cutter prior to measuring the actual depth of the leached layer of each sample cutter.

4. The method of claim 1, further comprising cleaning the leached layer of the polycrystalline diamond compact cutter to remove one or more by-product materials deposited within the leached layer during a leaching process that forms the leached layer.

5. The method of claim 1, wherein the multiple frequencies of the electrical signal range between approximately 0 Hertz and approximately 10 Megahertz.

6. A method of characterizing a quality of a polycrystalline structure, the method comprising:
   obtaining a leached component comprising the polycrystalline structure, the polycrystalline structure comprising a leached layer and an unleached layer, the unleached layer positioned adjacent to the leached layer, the leached layer having at least a portion of a catalyst material removed from therein;
   measuring capacitance values of the leached component at multiple frequencies of an electrical signal, the electrical signal provided to the leached component by a capacitance measuring device,
   wherein each capacitance value of the capacitance values is measured at a respective frequency of the multiple frequencies of the electrical signal;
   selecting a lowest capacitance value from among the measured capacitance values; and
   identifying an actual leaching depth value that corresponds to the selected lowest capacitance value using capacitance to leaching depth mapping information,
   wherein a depth of the leached layer of the leached component is estimated to equal the leaching depth value.

7. The method of claim 6, wherein the multiple frequencies of the electrical signal range between approximately 0 Hertz and approximately 10 Megahertz.

8. The method of claim 6, further comprising generating the leaching depth mapping information by:
   obtaining sample leached components;
   measuring capacitance values of each sample at the multiple frequencies of the electrical signal;
   cutting each sample to expose a cross-sectional surface of a leached layer thereof;
   measuring, using a distance measuring tool, an actual depth of the leached layer of each sample; and
   generating the leaching depth mapping information by associating, for each sample, a lowest capacitance value of the capacitance values of the particular sample with the actual leaching depth of the leached layer of the particular sample.

9. A system for measuring capacitance of a polycrystalline diamond compact cutter, the system comprising:
   a capacitance measuring device comprising a first terminal and a second terminal;
   the polycrystalline diamond compact cutter having a leached layer and an unleached layer adjacent to the leached layer, the leached layer having at least a portion of a catalyst material removed from therein;
   a first wire for electrically coupling the first terminal to a first surface of the polycrystalline diamond compact cutter; and
   a second wire for electrically coupling the second terminal to a second surface of the polycrystalline diamond compact cutter, the first surface and the second surface being on opposite sides of the leached layer and the first surface being a surface of the leached layer;
   a press for firmly engaging the wires with the respective surfaces to form a circuit,
   wherein the capacitance measuring device is operable to:
      provide an electrical signal to the polycrystalline diamond compact cutter to measure capacitance values of the polycrystalline diamond compact cutter,
      measure the capacitance values of the polycrystalline diamond compact cutter at multiple frequencies of the electrical signal,
      select a lowest capacitance value from anion, the measured capacitance values, and
      determine a leaching depth value that corresponds to the selected lowest capacitance value using capacitance to leaching depth mapping information.

10. The system of claim 9, further comprising:
   a first cap coupled to the first surface of the polycrystalline diamond compact cutter; and
   a second cap coupled to the second surface of the polycrystalline diamond compact cutter, wherein a portion of the polycrystalline diamond compact cutter including the second surface is positioned in a cavity of the second cap,
   wherein the first wire is electrically coupled to the first cap, and
   wherein the second wire is electrically coupled to the second cap.

11. The system of claim 10, wherein the first cap has an electrically conductive surface and an electrically insulated surface.

12. The system of claim 11, wherein the electrically conductive surface of the first cap is in physical contact with the first surface of the polycrystalline diamond compact cutter.

13. The system of claim 12, wherein the electrically conductive surface of the first cap has a ring shape.

14. The system of claim 9, wherein the multiple frequencies of the electrical signal range between approximately 0Hertz and approximately 10 Megahertz.

* * * * *